US012779032B2

(12) United States Patent
Khanna et al.

(10) Patent No.: US 12,779,032 B2
(45) Date of Patent: Nov. 3, 2026

(54) ADOPTIVE IMMUNOTHERAPY

(71) Applicant: The Council of the Queensland Institute of Medical Research, Herston (AU)

(72) Inventors: Rajiv Khanna, Brisbane (AU); Debottam Sinha, Brisbane (AU)

(73) Assignee: The Council of the Queensland Institute of Medical Research, Herston (AU)

( * ) Notice: Subject to any disclaimer, the term of this patent is extended or adjusted under 35 U.S.C. 154(b) by 1046 days.

(21) Appl. No.: 17/771,375

(22) PCT Filed: Oct. 23, 2020

(86) PCT No.: PCT/AU2020/051147

§ 371 (c)(1),
(2) Date: Apr. 22, 2022

(87) PCT Pub. No.: WO2021/077175

PCT Pub. Date: Apr. 29, 2021

(65) Prior Publication Data

US 2023/0210984 A1 Jul. 6, 2023

(30) Foreign Application Priority Data

Oct. 23, 2019 (AU) ................................ 2019903995

(51) Int. Cl.

| | |
|---|---|
| ***A61K 39/245*** | (2006.01) |
| ***A61K 31/4184*** | (2006.01) |
| ***A61K 31/519*** | (2006.01) |
| ***A61K 31/551*** | (2006.01) |
| ***A61K 40/11*** | (2025.01) |
| ***A61K 40/46*** | (2025.01) |
| ***A61K 40/50*** | (2025.01) |
| ***A61P 31/22*** | (2006.01) |
| ***A61P 35/00*** | (2006.01) |
| ***C12N 5/0783*** | (2010.01) |

(52) U.S. Cl.

CPC ........ *A61K 39/245* (2013.01); *A61K 31/4184* (2013.01); *A61K 31/519* (2013.01); *A61K 31/551* (2013.01); *A61K 40/11* (2025.01); *A61K 40/46* (2025.01); *A61P 31/22* (2018.01); *A61P 35/00* (2018.01); *C12N 5/0636* (2013.01); *C12N 5/0638* (2013.01); *A61K 40/50* (2025.01); *A61K 2239/38* (2023.05); *A61K 2239/48* (2023.05)

(58) Field of Classification Search

CPC .............. A61K 39/245; A61K 31/4184; A61K 31/519; A61K 31/551; A61K 40/11; A61K 40/46; A61K 40/50; A61K 2239/38; A61K 2239/48; A61K 38/00; A61K 2239/30; A61K 2239/51; A61K 39/12; A61K 39/39591; A61K 45/06; A61K 35/17; A61K 39/0011; A61K 2039/5158; A61K 2300/00; A61K 39/39533; A61K 2039/505; A61P 31/22; A61P 35/00; C12N 5/0636; C12N 5/0638; C12N 2710/16234; C12N 2501/2302; C12N 2710/16233; C07K 2317/21; C07K 2317/76; C07K 16/2818; C07K 16/2803

See application file for complete search history.

(56) References Cited

U.S. PATENT DOCUMENTS

2015/0017136 A1* 1/2015 Galetto .................. A61P 37/02 435/325
2018/0125891 A1* 5/2018 O'Reilly ................ A61K 40/46

FOREIGN PATENT DOCUMENTS

WO WO-2018106595 A1 * 6/2018 ........... A61K 31/444

OTHER PUBLICATIONS

Khanna R. Kissing the Epstein-Barr virus goodbye? https://www.science.org.au/curious/people-medicine/epstein-barr-virus. Australian Academy of Science. Last updated Jun. 24, 2015. (Year: 2015).*
ClinicalTrials Study Record ID NCT02973113. Nivolumab With Epstein Barr Virus Specific T Cells (EBVSTS), Relapsed/Refractory EBV Positive Lymphoma (PREVALE) (PREVALE). Heslop, H. Baylor College of Medicine. First Posted: Nov. 25, 2016. (Year: 2016).*
Lee et al., "Current concepts in the diagnosis and management of cytokine release syndrome," Blood. 124(2):188-195. (May 2014).
Cheng and Tian, "Current Development Status of MEK Inhibitors," Molecules. 22(10):1551. (20 pages). Sep. 2017.
Doroshow, et al., "BET inhibitors: a novel epigenetic approach," Annals of Oncology. 28(8):1776-1787. (Jul. 2017).

* cited by examiner

*Primary Examiner* — Rachel B Gill
(74) *Attorney, Agent, or Firm* — Clark + Elbing LLP

(57) ABSTRACT

Provided herein is the use of a first population of allogeneic T-cells recognizing a first EBV epitope, and a second allogenic population recognizing a second EBV epitope in the treatment of EBV-associated disorders. Also disclosed is the use of a population of allogeneic T-cells recognizing an EBV antigen in combination with a further therapeutic agent such as an immunotherapeutic agent, a MAPK, BET or MEK pathway inhibitor for treating EBV-associated disease.

13 Claims, 22 Drawing Sheets

A

ADOPTIVE IMMUNOTHERAPY

RELATED APPLICATIONS

This application claims priority to Australian Provisional Application No. 2019903995 entitled "Adoptive Immunotherapy", filed on 23 Oct. 2019, the entire content of which is hereby incorporated by reference in its entirety.

TECHNICAL FIELD

This invention relates generally to the field of therapeutic compositions, and methods of adoptive immunotherapy. More particularly, this invention relates to methods of adoptive immunotherapy in subjects with an Epstein-Barr virus (EBV)-associated disease, disorder or condition, such as cancer.

BACKGROUND OF THE INVENTION

Adoptive or cellular immunotherapy has emerged as a powerful tool for treating cancer, infectious complications and autoimmune diseases [1]. The first success of T cell therapy in clinic was demonstrated by Steven Rosenberg's group who pioneered in vitro expansion of patient derived tumour-infiltrating cells (TILs) and infused back into advanced stage melanoma patients [2]. Since then, the T cell effector function has been known to demonstrate clinical success against the treatment of drug resistance bacterial and fungal infection [3], viral infections including HIV [4], CMV [5] and BKV [6]; alongside hematological malignancies and EBV-associated post-transplant lymphoproliferative disease (PTLD) in hematopoietic stem cell transplant (HSCT) and solid organ transplant (SOT) patients [7]. However, the impact of these therapies in gaining an effective and sustained clinical response against solid cancers remains a significant challenge.

The mechanism of action associated with effective adoptive cell transfer (ACT) response against cancer revolves around the capacity of T cells to recognize tumour associated antigens (TAAs) presented by HLA molecules expressed on malignant cells [1]. The TAAs comprise of molecular factors which play critical role in cell proliferation, neoantigens arising from somatic mutations and cancer testes/germline antigens (CTA) which are located at immune privileged sites. In vitro expanded T cells from tumour-infiltrating lymphocytes or peripheral blood mononuclear cells have been extensively used. This technique has gained much attention against the treatment of viral-associated cancers and disease of transplant patients. In particular, adoptive T cell therapy has shown remarkable clinical responses against Epstein Barr Virus (EBV) associated posttransplant lymphomas (PTLD) [7]. EBV is a potent human ubiquitous B-lymphotropic oncogenic herpesvirus known to be associated with a wide range of human malignancies.

In healthy individuals, the EBV infection is controlled immunologically via functional $CD8^+$ cytotoxic T lymphocytes (CTL) and $CD4^+$ T lymphocytes predominantly recognizing EBNA3-6 antigens expressed in virus-infected B cells [8, 9]. However, due to its ubiquitous nature and persuasive cellular transforming capability, EBV infection is associated with multiple malignancies of both B cell and epithelial cell origin, such as Burkitt's lymphoma (BL), Hodgkin's lymphoma (HL), natural killer or T (NK/T) cells lymphoma, post-transplant lymphoproliferative disease (PTLD), nasopharyngeal carcinoma (NPC) and gastric carcinoma (GC) [10]. To date, radiation and/or chemotherapy remain the primary mainstay for the therapeutic treatment of EBV-associated malignancies. A large number of clinical trials are currently underway using EBV-specific autologous T cell immunotherapy [7]. However, time span required to manufacture and test the safety of autologous CTL prior to administration into the patient has been one of the major limitations on the generation of EBV-specific T cells for ACT.

SUMMARY OF THE INVENTION

The present invention is broadly directed to a method of treating or preventing an EBV-associated disease, disorder or condition, such as an EBV-associated cancer, in a subject by administering allogeneic EBV-specific T cells that bind or recognize an epitope of an EBV antigen thereto.

In a first aspect, the invention provides a method of treating or preventing an EBV-associated disease, disorder or condition in a subject, said method including the steps of:

(a) administering to the subject a first population of allogeneic T cells that bind or recognize a first epitope of an EBV antigen; and (b) administering to the subject a second population of allogeneic T cells that bind or recognize a second epitope of the EBV antigen or a further EBV antigen;

to thereby treat or prevent the EBV-associated disease, disorder or condition in the subject.

In some embodiments, the method of the present aspect further includes the initial step of generating the first and/or second populations of allogeneic T cells in vitro.

Suitably, the present method includes the further step of administering a therapeutic agent to the subject. In one embodiment, the therapeutic agent is selected from the group consisting of an immunotherapeutic agent, a MAPK pathway inhibitor, such as a MEK1/2 inhibitor, a BET inhibitor and any combination thereof. In this regard, the immunotherapeutic agent suitably is or comprises an immune checkpoint inhibitor, such as a PD1 inhibitor, a PDL1 inhibitor, a CTLA4 inhibitor, a LAG3 inhibitor, a TIM3 inhibitor or a CD96 inhibitor. In some particular embodiments, the immune checkpoint inhibitor is or comprises an anti-PD1 antibody.

In a second aspect, the invention resides in a pharmaceutical composition for treating or preventing an EBV-associated disease, disorder or condition in a subject, the composition comprising:

a first population of allogeneic T cells that bind or recognize a first epitope of an EBV antigen;

a second population of allogeneic T cells that bind or recognize a second epitope of the EBV antigen or a further EBV antigen; and optionally a pharmaceutically acceptable carrier, diluent and/or excipient.

With respect to the aforementioned aspects, the first population of allogeneic T cells and cells of the EBV-associated disease, disorder or condition suitably both comprise or are restricted by a first human leukocyte antigen (HLA) allele that encodes a first MHC protein. In this regard, the first MHC protein may present the first epitope of the EBV antigen on cells of the EBV-associated disease, disorder or condition.

For the first and second aspects, the second population of allogeneic T cells and cells of the EBV-associated disease, disorder or condition both comprise or are restricted by a second HLA allele that encodes a second MHC protein. To this end, the second MHC protein suitably presents the second epitope of the EBV antigen or the further EBV antigen on cells of the EBV-associated disease, disorder or condition.

In some embodiments of the aforementioned aspects, the second population of allogeneic T cells is administered prior to, simultaneously with and/or subsequent to administration of the first population of allogeneic T cells.

In a third aspect, the invention resides in a method of treating or preventing an EBV-associated disease, disorder or condition in a subject, said method including the steps of:

(a) administering to the subject a population of allogeneic T cells that bind or recognize an epitope of an EBV antigen; and (b) administering to the subject a therapeutic agent, wherein the therapeutic agent is selected from the group consisting of an immunotherapeutic agent, a MAPK pathway inhibitor, a BET inhibitor and any combination thereof;

to thereby treat or prevent the EBV-associated disease, disorder or condition in the subject.

Suitably, the population of allogeneic T cells is administered prior to, simultaneously with and/or subsequent to administration of the therapeutic agent.

In some embodiments, the current method further includes the initial step of generating the population of allogeneic T cells in vitro.

In a fourth aspect, the invention provides a pharmaceutical composition for treating or preventing an EBV-associated disease, disorder or condition in a subject, the composition comprising:

a population of allogeneic T cells that bind or recognize an epitope of an EBV antigen;

a therapeutic agent, wherein the therapeutic agent is selected from the group consisting of an immunotherapeutic agent, a MAPK pathway inhibitor, a BET inhibitor and any combination thereof; and optionally, a pharmaceutically acceptable carrier, diluent and/or excipient.

Referring to the third and fourth aspects, the population of allogeneic T cells and cells of the EBV-associated disease, disorder or condition suitably both comprise or are restricted by a first human leukocyte antigen (HLA) allele that encodes a first MHC protein. In some embodiments, the MHC protein presents the epitope of the EBV antigen on cells of the EBV-associated disease, disorder or condition.

Suitably for the third and fourth aspects, the immunotherapeutic agent is or comprises an immune checkpoint inhibitor, such as a PD1 inhibitor, a PDL1 inhibitor, a CTLA4 inhibitor, a LAG3 inhibitor, a TIM3 inhibitor or a CD96 inhibitor. In certain embodiments, the immune checkpoint inhibitor is or comprises an anti-PD1 antibody. In some embodiments, the MAPK pathway inhibitor is or comprises a MEK1/2 inhibitor.

In a fifth aspect, the invention relates to use of a first population of allogeneic T cells that bind or recognize a first epitope of an EBV antigen in the manufacture of a medicament for the treatment or prevention of an EBV-associated disease, disorder or condition in a subject; wherein the first population of allogeneic T cells is to be administered in combination with: (a) a second population of allogeneic T cells that bind or recognize a second epitope of the EBV antigen or a further EBV antigen; and/or (b) a therapeutic agent, wherein the therapeutic agent is selected from the group consisting of an immunotherapeutic agent, a MAPK pathway inhibitor, a BET inhibitor and any combination thereof.

In a sixth aspect, the invention provides a first population of allogeneic T cells that bind or recognize a first epitope of an EBV antigen for use in the treatment or prevention of an EBV-associated disease, disorder or condition in a subject; wherein the first population of allogeneic T cells is to be administered in combination with: (a) a second population of allogeneic T cells that bind or recognize a second epitope of the EBV antigen or a further EBV antigen; and/or (b) a therapeutic agent, wherein the therapeutic agent is selected from the group consisting of an immunotherapeutic agent, a MAPK pathway inhibitor, a BET inhibitor and any combination thereof.

Referring to the aforementioned aspects, the EBV antigen and/or the further EBV antigen is suitably selected from the group consisting of EBNA1, EBNA2, EBNA3A, EBNA3B, EBNA3C, LMP1, LMP2 and any combination thereof. In one embodiment, the EBV antigen and/or the further EBV antigen is or comprises EBNA1, LMP1 and/or LMP2.

Suitably for the above aspects, the EBV-associated disease, disorder or condition is or comprises an EBV-associated cancer. In certain embodiments, the EBV-associated cancer is selected from the group consisting of nasopharyngeal carcinoma, NKT cell lymphoma, Hodgkin's Lymphoma, post-transplant lymphoproliferative disease, Burkitt's lymphoma, Diffuse large B-cell lymphoma, gastric cancer, and any combination thereof.

Suitably, the subject of the aforementioned aspects of the invention is a mammal.

Preferably, the subject is a human.

Throughout this specification, unless otherwise indicated, "comprise", "comprises" and "comprising" are used inclusively rather than exclusively, so that a stated integer or group of integers may include one or more other non-stated integers or groups of integers.

It will also be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

DETAILED DESCRIPTION OF THE INVENTION

Figure 1:
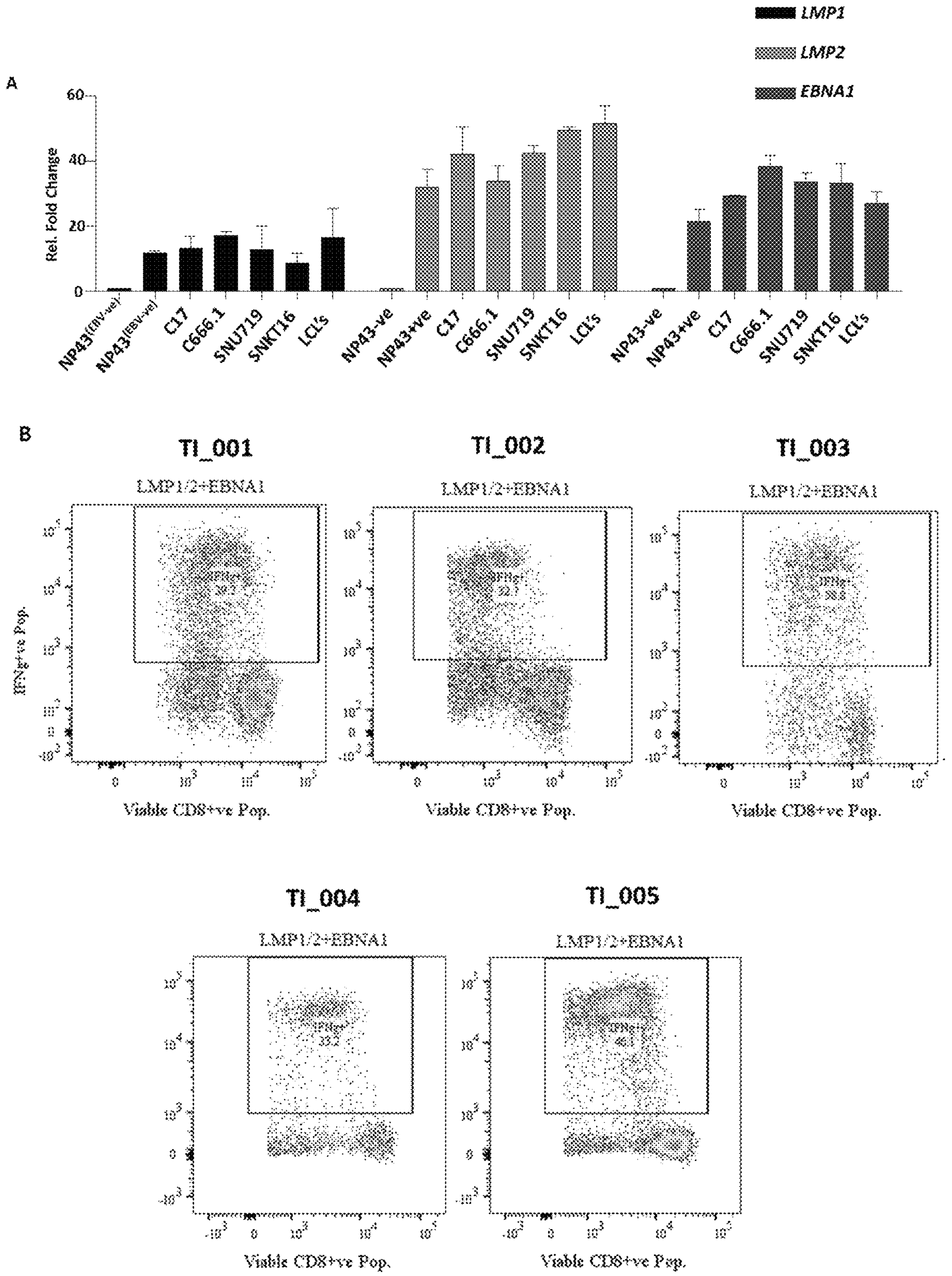
FIG. 1: Efficacy of allogenic "off-the-shelf" EBV specific T-cells in recognizing and eliminating multiple cancers in vitro. (A) Statistical representation of the relative fold expression at transcript level of indicated EBV-associated genes across respective EBV-associated cancer cell lines compared to NP43 (EBV−) cancer cells. Housekeeping genes, HPRT1 and 18s RNA was used as loading control. (B) FACS plot representing expression of IFN-γ in presence of LMP1/2 and EBNA1 specific peptides observed in the viable CD8+ population across indicated allogenic EBV-specific effector AdE1-LMPpoly transfected T cells as previously described [1]. (C) Statistical representation of cellular cytotoxicity measured by LDH release assay among indicated EBV-associated cancer cell lines highlighting the dose-dependent increase of T cell derived cytotoxicity across varying effector to target cell ratio (5:1-100:1). The cellular cytotoxicity of the HLA-matched T cells is represented as a relative fold change of LDH release after 24 hours of T cell treatment of cancer cells compared to the positive control (detergent lysed control). (D) Statistical representation of the cell viability measured by MTS assay highlighting the impact of a HLA-matched T cells in suppressing cellular growth of multiple EBV-associated cancer cell lines of different origin in a dose-dependent manner across varying effector to target cell ratio (5:1-100:1). SNKT16 (HLA) was treated with both TI_001 and TI_002 and its cell viability was compared to the cell viability SNU719 (HLA) and C17(HLA) respectively. The cell viability of the respective cancer cells is represented as a relative fold change of viable cells after 24 hours of T cell treatment compared to mock (PBS) treated control. (E) Statistical representation of cell death measured by Annexin V binding assay among indicated EBV-associated cancer cell lines in the presence of HLA-matched T cell (50:1 effector to target cell ratio). The cell death among respective cancer cells is represented as the relative fold change of Annexin V binding in T cells treated samples compared to mock (PBS) treated, after 48 hours of T cell treatment. Error bars represent the ±SEM from three independent experiments.
Figure 1:
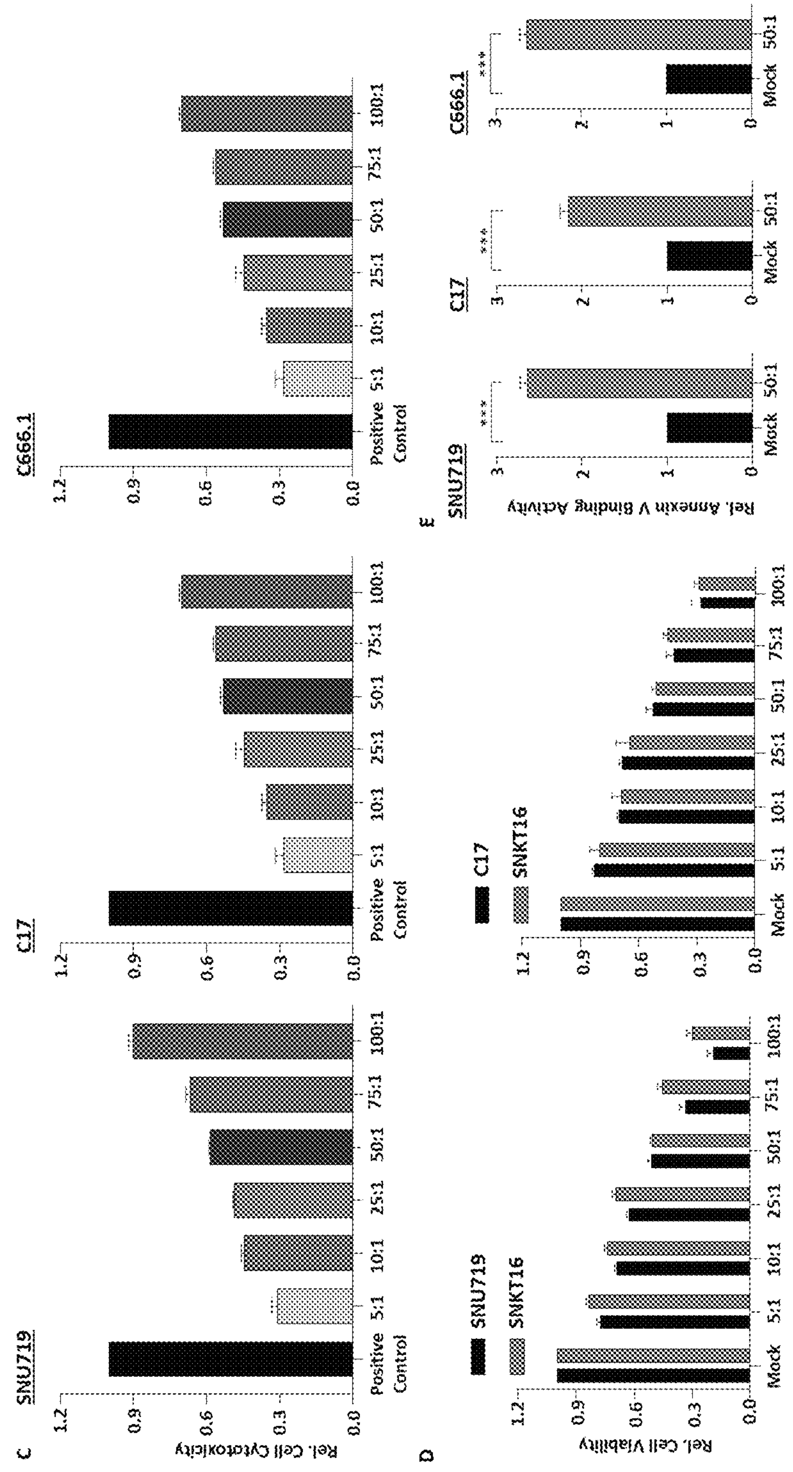

The present invention is at least partly predicated on the surprising discovery that adoptive immunotherapy with "off-the-shelf" allogeneic EBV-specific T-cells is capable of treating or preventing a range of EBV-associated or EBV-positive cancers. This therapeutic effect has been shown to be particularly effective when a combination of EBV-specific T cell populations that are specific for different EBV antigen epitopes are used. Additionally, the present inventors have demonstrated that the combination of allogeneic EBV-specific T cells and an immune checkpoint inhibitor, a MEK1/2 inhibitor and/or a BET inhibitor could significantly improve the efficacy of such adoptive T cell therapy against EBV-associated diseases, disorders or conditions.

Accordingly, in a broad form, the present invention relates to a method of treating or preventing an EBV-associated disease, disorder or condition in a subject, said method including the step of administering a population of allogeneic T cells that bind or recognize an epitope of an EBV antigen to the subject to thereby treat or prevent the EBV-associated disease, disorder or condition in the subject.

In an aspect, the present invention relates to a method of treating or preventing an EBV-associated disease, disorder or condition in a subject, said method including the steps of:

(a) administering to the subject a therapeutically effective amount of a first population of allogeneic T cells that bind or recognize a first epitope of an EBV antigen; and (b) administering to the subject a therapeutically effective amount of a second population of allogeneic T cells that bind or recognize a second epitope of the EBV antigen or a further EBV antigen;

to thereby treat or prevent the EBV-associated disease, disorder or condition in the subject.

In a related aspect, the invention provides a pharmaceutical composition for treating or preventing an EBV-associated disease, disorder or condition in a subject, the composition comprising:

a first population of allogeneic T cells that bind or recognize a first epitope of an EBV antigen;

a second population of allogeneic T cells that bind or recognize a second epitope of the EBV antigen or a further EBV antigen; and optionally a pharmaceutically acceptable carrier, diluent and/or excipient.

The statements which follow apply equally to the two aforementioned aspects.

Epstein-Barr Virus or EBV is a common human pathogen and may cause, or be associated with, one or more diseases, disorders or conditions in humans. Thus, certain embodiments of the aforementioned methods relate to preventing and/or treating one or more diseases, disorders or conditions caused by, or associated with, an EBV infection in humans, such as an EBV-associated cancer. EBV predominantly infects human hosts through epithelial cells and B lymphocytes where it can then establish long-term latency in the human host. Primary infection of EBV causes over 90% of cases of infectious mononucleosis (IM) worldwide, infecting mainly children and young adults through the expansion of EBV infected B cells. EBV has also been associated with several cancers, including Burkitt and Hodgkin's lymphomas, gastric and nasopharyngeal carcinomas, lymphomas in HIV-infected individuals and post-transplant lymphoproliferative disorder (PTLD). EBV has also been found to be implicated in autoimmune diseases, particularly multiple sclerosis.

In the context of the present invention, by "EBV-associated disease, disorder or condition" is meant any clinical pathology resulting from or link to an infection by an Epstein Barr virus. To this end, EBV-associated disease, disorder or condition can mean any disease caused, directly or indirectly, by EBV as well as diseases which predispose a patient to infection by EBV. Examples of diseases falling into the former category include infectious mononucleosis, nasopharyngeal carcinoma, and Burkitt's lymphoma. Diseases in the latter category (i.e., those which place the patient at risk of EBV infection) include acquired immune deficiency syndrome and, generally, any condition that causes a state of immunosuppression or decreased function of the immune system such as patients who receive organ transplants and certain cancer therapies. In one particular embodiment, the EBV-associated disease, disorder or condition suitably is or comprises multiple sclerosis.

The term "EBV-positive cells" refers to those cells, inclusive of cancer cells, which express EBV or one or more EBV proteins, such as in a latent form.

In preferred embodiments, the EBV-associated disease, disorder or condition is or comprises an EBV-associated and/or -positive cancer. As used herein, and unless otherwise specified, the term "EBV-associated cancer" or "EBV-positive cancer" refers to a cancer that has been linked to the Epstein-Barr virus (EBV). In certain embodiments, EBV-positive cancers are cancers wherein greater than about 30%, greater than about 40%, greater than about 50%, greater than about 60%, greater than about 70%, or greater than about 80% contain or express the EBV virus.

As generally used herein, the terms "cancer", "tumour", "malignant" and "malignancy" refer to diseases or conditions, or to cells or tissues associated with the diseases or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumour markers, loss of tumour suppressor expression or activity and/or aberrant or abnormal cell surface marker expression.

Cancers may include any aggressive or potentially aggressive cancers, tumours or other malignancies such as listed in the NCI Cancer Index, including all major cancer forms such as sarcomas, carcinomas, lymphomas, leukaemias and blastomas, although without limitation thereto. These may include breast cancer, lung cancer inclusive of lung adenocarcinoma, cancers of the reproductive system inclusive of ovarian cancer, cervical cancer, uterine cancer and prostate cancer, cancers of the brain and nervous system, head and neck cancers, gastrointestinal cancers inclusive of colon cancer, colorectal cancer and gastric cancer, liver cancer, kidney cancer, skin cancers such as melanoma and skin carcinomas, blood cell cancers inclusive of lymphoid cancers and myelomonocytic cancers, cancers of the endocrine system such as pancreatic cancer and pituitary cancers, musculoskeletal cancers inclusive of bone and soft tissue cancers, although without limitation thereto. In particular embodiments, the cancer is a solid cancer or a leukaemia or liquid cancer. Suitably, the cancer expresses, such as overexpresses, one or more EBV antigens, such as those hereinbefore described.

In particular embodiments, the EBV-associated cancer is selected from the group consisting of nasopharyngeal carcinoma, NKT cell lymphoma, Hodgkin's Lymphoma, post-transplant lymphoproliferative disease, Burkitt's lymphoma, Diffuse large B-cell lymphoma, gastric cancer, parotid carcinoma, breast carcinoma, leiomyosarcoma and any combination thereof. In a specific embodiment, the EBV-associated cancer is not post-transplant lymphoproliferative disease.

As used herein, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in recombinant, chemical synthetic, enriched, purified or partially purified form.

As used herein, "treating", "treat" or "treatment" refers to a therapeutic intervention that at least partly ameliorates, eliminates or reduces a symptom or pathological sign of an EBV-associated disease, disorder or condition after it has begun to develop. Treatment need not be absolute to be beneficial to the subject.

As used herein, "preventing", "prevent" or "prevention" refers to a course of action initiated prior to infection by, or exposure to, EBV or molecular components thereof and/or before the onset of a symptom or pathological sign of an EBV-associated disease, disorder or condition, so as to at least partly prevent and/or reduce the symptom or pathological sign. It is to be understood that such prevention need not be absolute or complete to be beneficial to a subject.

The term "therapeutically effective amount" describes a quantity of a specified agent, such as EBV-specific allogeneic T cells or therapeutic agent, sufficient to achieve a desired effect in a subject being treated with that agent. For example, this can be the amount of a composition comprising the first population of allogeneic T cells, the second population of allogeneic T cells and/or the therapeutic agent described herein, necessary to reduce, alleviate and/or prevent an EBV-associated disease, disorder or condition, inclusive of EBV-associated cancer, cancer metastasis and recurrence. In some embodiments, a "therapeutically effective amount" is sufficient to reduce or eliminate a symptom of an EBV-associated disease, disorder or condition. In other embodiments, a "therapeutically effective amount" is an amount sufficient to achieve a desired biological effect, for example, an amount that is effective to decrease or prevent EBV-associated cancer growth, recurrence and/or metastasis.

Ideally, a therapeutically effective amount of an agent is an amount sufficient to induce the desired result without causing a substantial cytotoxic effect in the subject. The effective amount of an agent useful for reducing, alleviating and/or preventing an EBV-associated disease, disorder or condition will be dependent on the subject being treated, the type and severity of any associated disease, disorder and/or condition (e.g., the type of EBV-associated disease, disorder or condition), and the manner of administration of the therapeutic composition.

It will be appreciated that the method of the present aspect may include one or more further treatments, such as cancer treatments, in addition to those recited above. Such treatments may include drug therapy, chemotherapy, antibody, nucleic acid and other biomolecular therapies, radiation therapy, surgery, nutritional therapy, relaxation or meditational therapy and other natural or holistic therapies, although without limitation thereto. Generally, drugs, biomolecules (e.g., antibodies, inhibitory nucleic acids such as siRNA) or chemotherapeutic agents are referred to herein as "anti-cancer therapeutic agents" or "anti-cancer agents".

By "administering" or "administration" is meant the introduction of an allogeneic T cell and/or therapeutic agent or composition disclosed herein into an animal subject by a particular, chosen route.

Administration of the allogeneic T cells and/or therapeutic agents, or a composition comprising same may be by any known parenteral, topical or enteral route inclusive of intravenous, intramuscular, intraperitoneal, intracranial, transdermal, oral, intranasal, anal and intra-ocular, although without limitation thereto.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy, but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The allogeneic T cells, therapeutic agents and compositions described herein may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

In certain embodiments, the methods of treating an EBV-associated disease, disorder or condition as described herein comprise administering at least 2 doses (e.g., 2, 3, 4, 5, 6 etc doses) of the first and/or second populations of allogeneic T cells and or the therapeutic agents to the subject. Such doses may be administered in a periodic manner, such as daily, weekly, fortnightly, monthly etc as required.

One particular broad application of the present invention is the provision of methods of performing cellular or adoptive immunotherapy in a subject having an EBV-associated disease, disorder or condition, such as those hereinbefore described, said method including the step of administering a therapeutically effective amount of an allogeneic T cell described herein and optionally a pharmaceutically acceptable carrier, diluent or excipient to the subject.

The terms "cellular immunotherapy" or "adoptive immunotherapy" denote the transfer of immunocompetent cells, such as T-cells, for the treatment of cancer or infectious diseases (see, e.g., June, C. H., ed., 2001, In: Cancer Chemotherapy and Biotherapy: Principles and Practice, Lippincott Williams & Wilkins, Baltimore; Vonderheide et al., 2003, Immun. Research 27:1-15). To this end, it will be understood that adoptive immunotherapy is a strategy typically aimed at replacing, repairing, or enhancing the biological function of a tissue or system, such as the immune system, by means of autologous or allogeneic cells, such as T-cells.

As used herein, the term "allogeneic" refers to cells or tissues, such as T cells, derived from individuals belonging to the same species but genetically different, and are therefore generally immunologically incompatible. Thus, the term "allogeneic cells" refers to cell types that are antigenically distinct, yet belonging to the same species. Typically, the term "allogeneic" is used to define cells, such as T cells, that are transplanted from a donor to a recipient of the same species.

As used herein, the term "T cell" (i.e., T lymphocyte) is intended to include all cells within the T cell lineage, including thymocytes, immature T cells, mature T cells and the like, from a mammal (e.g., human). The various T cell populations, such as helper T cells, regulatory T cells, cytotoxic T cells, natural killer T cells and memory T cells, can be defined based on their cytokine profiles and their function. Preferably, T cells are mature T cells that express either CD4 or CD8, but not both, and a T cell receptor. It will be understood that a T cell receptor (TCR) is the molecule found on the surface of T cells that is responsible for recognizing antigenic peptides bound to MHC or HLA molecules. Suitably, the allogeneic T cells comprise CD4+ helper T cells and/or a CD8+ cytotoxic T cells. In this regard, the allogeneic T-cells described herein may be in a mixed population of CD4+ helper T cell/CD8+ cytotoxic T cells.

According to the invention, a population of allogeneic T cells, such as a first and/or second population of allogeneic T cells, comprising EBV-specific T cells is administered to the human patient. The population of allogeneic T cells that is administered to the human patient is suitably restricted by an HLA allele shared with EBV-positive cells of the EBV-associated disease, disorder or condition. In one particular embodiment, the first population of allogeneic T cells and cells of the EBV-associated disease, disorder or condition both comprise, share or are restricted by a first human leukocyte antigen (HLA) allele that encodes a first MHC protein. In another embodiment, the second population of allogeneic T cells and cells of the EBV-associated disease, disorder or condition both comprise or are restricted by a second HLA allele that encodes a second MHC protein. In some embodiments, this HLA allele restriction is ensured by ascertaining the HLA assignment of cells, such as cancer cells, of the EBV-associated disease, disorder or condition, and selecting a population of allogeneic T cells comprising EBV-specific T cells (or a T cell line from which to derive the population of allogeneic T cells) restricted by an HLA allele of such cells. The HLA assignment (i.e., the HLA loci type) can be ascertained (i.e., typed) by any method known in the art. Non-limiting exemplary methods for ascertaining the HLA assignment can be found in ASHI Laboratory Manual, Edition 4.2 (2003), which is incorporated by reference herein.

In certain embodiments, the first and/or second population of allogeneic T cells share one or more (e.g., 1, 2, 3, 4, 5, 6, 7, 8 HLA alleles) HLA alleles (e.g., HLA-A alleles, HLA-B alleles, HLA-C alleles, and/or HLA-DR alleles) with EBV-positive cells of the EBV-associated disease, disorder or condition. In this regard, it is envisaged that the first and second population of allogeneic T cells can share one or more of the same HLA alleles with cells of the EBV-associated disease, disorder or condition. Indeed, in particular embodiments, the first population of allogeneic T cells share one or more HLA alleles (e.g., 1, 2, 3, 4, 5, 6, 7, 8 HLA alleles) with the second population of allogeneic T cells. Ideally, the first population of allogeneic T cells suitably comprises one or more HLA alleles, such as the first HLA allele, that are shared with cells of the EBV-associated disease, disorder or condition that are also not shared with (i.e., are different to) those HLA alleles, such as the second HLA allele, of the second population of allogeneic T cells. Similarly, the second population of allogeneic T cells suitably comprises one or more HLA alleles, such as the second HLA allele, that are shared with cells of the EBV-associated disease, disorder or condition that are also not shared with (i.e., are different to) those HLA alleles, such as the first HLA allele, comprised by the first population of allogeneic T cells. To this end, the first and second population of allogeneic T cells preferably do not possess or comprise the same or identical complement of HLA alleles. Furthermore, the first population of allogeneic T cells suitably do not recognise or bind the second epitope and/or the second population of allogeneic T cells suitably do not recognise or bind the first epitope.

As used herein, the term "major histocompatibility complex" (MHC) refers to an antigen presentation molecule, protein or polypeptide that functions as part of the immune system to bind antigens and other peptide fragments and display them on the cell surface for recognition by antigen recognition molecules such as TCR. MHC may be used interchangeably with the term "human leukocyte antigen" (HLA) when used in reference to human MHC; thus, MHC refers to all HLA subtypes including, but not limited to, the classical MHC alleles or genes disclosed herein: HLA-A, HLA-B, HLA-C, HLA-E, HLA-F, HLA-G, HLA-DM, HLA-DO, HLA-DP, HLA-DQ, and HLA-DR, in addition to all variants, isoforms, isotypes, and other biological equivalents thereof. MHC class I (MHC-I) and MHC class II (MHC-II) molecules utilize distinct antigen processing pathways. In general, peptides derived from intracellular antigens are presented to CD8+ T cells by MHC class I molecules, which are expressed on virtually all cells, while extracellular antigen-derived peptides are presented to CD4+ T cells by MHC-II molecules. However, several exceptions to this general principle have been observed.

In certain embodiments disclosed herein, a particular EBV-specific antigen, peptide, and/or epitope is identified and presented in an antigen-MHC complex in the context of an appropriate MHC class I or II protein on cells of the EBV-associated disease, disorder or condition. By way of example, the first MHC protein suitably presents the first epitope of the EBV antigen on cells of the EBV-associated disease, disorder or condition for recognition by the first population of allogeneic T cells, whilst the second MHC protein can present the second epitope of the EBV antigen or the further EBV antigen on cells of the EBV-associated disease, disorder or condition for recognition by the second population of allogeneic T cells. In view of the foregoing, the genetic makeup of the allogeneic T cells described herein may be assessed to determine which HLA/MHC allele is suitable for a particular subject and/or EBV-associated disease, disorder or condition with a particular set of EBV antigens.

Suitably, the EBV antigen and/or the further EBV antigen may be any as are known in the art. Exemplary EBV antigens include the proteins EBNA1, EBNA2, EBNA3A, EBNA3B, EBNA3C, LMP1 and LMP2. In particular embodiments, the EBV antigen and/or the further EBV antigen is or comprises EBNA1, LMP1 and/or LMP2.

The allogeneic T cells described herein suitably have antigen specificity for the EBV antigen and/or the further EBV antigen. The phrases "have antigen specificity" and "elicit antigen-specific response" as used herein means that the allogeneic T cells can specifically bind to and immunologically recognize an antigen, such that binding of the allogeneic T cells to the antigen elicits an immune response. Without being bound to a particular theory or mechanism, it is believed that by eliciting an antigen-specific response against EBV-positive cells of the EBV-associated disease, disorder or condition, the EBV-specific allogeneic T cells described herein can provide for one or more of any of the following: targeting and destroying EBV-positive cells, such as EBV-positive cancer cells, reducing or eliminating cancer cells, facilitating infiltration of immune cells to tumour site(s), and enhancing/extending anti-cancer responses.

As generally used herein, an "epitope" is an antigenic protein fragment that comprises a continuous or discontinuous sequence of amino acids of a protein, wherein the epitope can be recognized or bound by an element of the immune system, such as an antibody or other antigen receptor, such as an MHC protein. It will be well understood by a skilled artisan that most EBV antigens can have multiple epitopes or antigenic determinants.

In view of the foregoing, the first epitope can be an antigenic protein fragment of an EBV protein, whilst the second epitope is suitably a different antigenic protein fragment from the same EBV protein from which the first epitope is derived or a further EBV protein.

As used herein a "protein" is an amino acid polymer, wherein the amino acids may include D-amino acids, L-amino acids, natural and/or non-natural amino acids. As typically used herein, a "peptide" is a protein comprising no more than sixty (60) contiguous amino acids. As typically used herein, a "polypeptide" is a protein comprising more than sixty (60) contiguous amino acids. The term "protein" should also be understood to encompass protein-containing molecules such as glycoproteins and lipoproteins, although without limitation thereto.

In some embodiments, the allogeneic T cells and/or the therapeutic agents described herein, inclusive of combinations of these, may be administered to a subject in the form of a composition comprising a pharmaceutically acceptable carrier, diluent or excipient.

It will be appreciated that pharmaceutically acceptable carriers, diluents and/or excipients may include any solid, semi-solid, gel or liquid fillers, diluents or encapsulating substances that may be safely used in systemic administration. Depending upon the particular route of administration, carriers, diluents and/or excipients may be selected from a group including sugars, starches, cellulose and its derivatives, malt, gelatine, talc, calcium sulphate, vegetable oils, synthetic oils, polyols, alginic acid, isotonic saline, pyrogen-free water, wetting or emulsifying agents, bulking agents, glidants, coatings (e.g., enteric coatings), emollients, binders, fillers, disintegrants, lubricants, pH buffering agents (e.g. phosphate buffers) and/or flavouring agents, although without limitation thereto. The composition may be administered to a human in any one or more dosage forms that include tablets, dispersions, suspensions, injectable solutions, syrups, troches, capsules, suppositories, aerosols, transdermal patches and the like.

A useful reference describing pharmaceutically acceptable carriers, diluents and excipients is Remington's Pharmaceutical Sciences (Mack Publishing Co. N.J. USA, 1991) which is incorporated herein by reference.

In particular embodiments, the second population of allogeneic T cells is administered (i) prior to; (ii) after; or (iii) simultaneously with, the administration of the first population of allogeneic T cells. In one embodiment, administration of the first population of allogeneic T cells, and administration of the second population of allogeneic T cells (either sequentially or concurrently) results in treatment or prevention of an EBV-associated disease, disorder or condition that is greater than such treatment or prevention from administration of either the first population of allogeneic T cells or the second population of allogeneic T cells in the absence of the other.

In particular embodiments, the above method further includes the initial step of generating the first and/or second populations of allogeneic T cells in vitro. The first and second populations of allogeneic T cells comprising EBV-specific T cells that are administered to the human patient can be generated by a method known in the art, or can be selected from a pre-existing bank (collection) of cryopreserved T cell lines (each T cell line comprising EBV-specific T cells) generated by a method known in the art, and thawed and preferably expanded prior to administration.

In certain embodiments, the step of generating the population of allogeneic T cells in vitro comprises sensitizing (i.e., stimulating) allogeneic T cells to one or more EBV antigens so as to produce EBV-specific T cells. The allogeneic T cells that are used for generating the population of allogeneic T cells in vitro can be isolated from the donor of the allogeneic T cells by any method known in the art. In a specific embodiment, the allogeneic T cells are enriched from peripheral blood lymphocytes separated from PBMCs of the donor of the allogeneic T cells.

In particular embodiments, the step of sensitizing allogeneic T cells loading or transforming an antigen presenting cell, such as dendritic cells, cytokine-activated monocytes, or peripheral blood mononuclear cells with at least one immunogenic peptide derived from one or more EBV antigens. To this end, the antigen presenting cell can be loaded or transformed with, for example, a pool of or a polytope comprising overlapping peptides derived from one or more EBV antigens. In one specific embodiment, the step of generating the population of allogeneic T cells in vitro comprises sensitizing allogeneic T cells using peripheral blood mononuclear cells.

Suitably, the aforementioned method includes the further step of administering a therapeutic agent to the subject. Similarly, the above composition may further include a therapeutic agent. As used herein, the term "therapeutic agent" refers to a compound or molecule used to image, affect, treat, address, prevent or ameliorate an undesirable condition or disease, such as an EBV-associated disease, disorder or condition in a subject.

The therapeutic agent may be any as are known in the art. In some embodiments, the therapeutic agent is or comprises an anti-cancer treatment or an anti-cancer agent. Generally, drugs, biomolecules (e.g., antibodies, inhibitory nucleic acids such as siRNA) or chemotherapeutic agents are referred to herein as "anti-cancer therapeutic agents". By way of example only, these may include: chemotherapeutic agents such as paclitaxel, doxorubicin, methotrexate, irinotecan, dacarbazine, temozolomide and cisplatin, although without limitation thereto; biotherapeutic or immunotherapeutic agents, such as anti-PD-1 antibodies (e.g., Nivolumab) and anti-CTLA4 antibodies (e.g., Ipilimumab), although without limitation thereto; and/or molecularly targeted agents such as MAPK pathway (i.e., Ras-Raf-MEK-ERK signalling) inhibitors and BET inhibitors.

In particular embodiments, the therapeutic agent is selected from the group consisting of an immunotherapeutic agent, a mitogen-activated protein kinase (MAPK) pathway inhibitor, a BET inhibitor and any combination thereof.

The term "immunotherapeutic agent" as used herein, refers to any agent that can induce, enhance, or suppress an immune response in a subject. In certain embodiments, an immunotherapeutic agent can be an immune checkpoint modulator. As used herein, the term "immune checkpoint modulator" refers to a molecule that can completely or partially reduce, inhibit, interfere with, or modulate one or more immune checkpoint proteins that regulate T-cell activation or function. In certain embodiments, the immune checkpoint modulator is an immune checkpoint inhibitor.

Non-limiting examples of immune checkpoint proteins include cytotoxic T-lymphocyte-associated antigen (CTLA; e.g., CTLA4) and its ligands CD 80 and CD86; programmed cell death protein (PD, e.g., PD-1) and its ligands and PDL2; indoleamine-pyrrole 2,3-dioxygenase-1 (ID01); T cell membrane protein (TIM, e.g., TIM3); adenosine A2a receptor (A2aR); lymphocyte activation gene (LAG, e.g., LAG3); killer immunoglobulin receptor (KIR); CD96; and the like. It will be appreciated that these proteins are typically responsible for co-stimulatory or inhibitory T-cell responses. Immune checkpoint proteins can broadly regulate and maintain self-tolerance and the duration and amplitude of physiological immune responses.

In certain embodiments, an immune checkpoint modulator (e.g., an immune checkpoint inhibitor) can be a small molecule, an antibody, a recombinant binding protein, or a peptide that binds to or inhibits a biological activity of an immune checkpoint protein.

Non-limiting examples of immune checkpoint modulators (e.g., immune checkpoint inhibitors) include CTLA4 inhibitors (e.g., Ipilimumab), PD1 inhibitors (e.g., nivolumab), PDL1 inhibitors (e.g., Atezolizumab, Avelumab, Durvalumab), LAG3 inhibitors, KIR inhibitors, B7-H3 ligands, B7-H4 ligands, CD96 inhibitors and TIM3 inhibitors. In particular embodiments, the immune checkpoint inhibitor is selected from the group consisting of an anti-PD1 antibody, an anti-PDL1 antibody, an anti-CTLA4 antibody, an anti-LAG3 antibody, an anti-TIM3 antibody, an anti-CD96 antibody and any combination thereof.

In one particular embodiment, the immune checkpoint inhibitor is or comprises a PD1 inhibitor, and more particularly an anti-PD1 antibody. Exemplary PD1 inhibitors and anti-PD1 antibodies include Pembrolizumab, Nivolumab, Cemiplimab, Spartalizumab, Camrelizumab, Sintilimab, Tislelizumab, Toripalimab, AMP-224 and AMP-514.

As used herein, an "antibody" is or comprises an immunoglobulin protein, inclusive of fragments thereof. The term "immunoglobulin" includes any antigen-binding protein product of a mammalian immunoglobulin gene complex, including immunoglobulin isotypes IgA, IgD, IgM, IgG and IgE and antigen-binding fragments thereof. Included in the term "immunoglobulin" are immunoglobulins that are recombinant, chimeric or humanized or otherwise comprise altered or variant amino acid residues, sequences and/or glycosylation, whether naturally occurring or produced by human intervention (e.g., by recombinant DNA technology).

The invention also includes within its scope antibody fragments, such as Fc, Fab or F(ab)2 fragments or single chain Fv antibodies (scFvs). The invention is also contemplated to include multivalent recombinant antibody fragments, so-called diabodies, triabodies and/or tetrabodies, comprising a plurality of scFvs, as well as dimerisation-activated demibodies (e.g., WO/2007/062466). By way of example, such antibodies may be prepared in accordance with the methods described in Holliger et al., 1993 Proc Natl Acad Sci USA 90:6444-6448; or in Kipriyanov, 2009 Methods Mol Biol 562:177-93 and herein incorporated by reference in their entirety.

Generally, antibodies and antibody fragments may be polyclonal or monoclonal. It will also be appreciated that antibodies may be produced as recombinant synthetic antibodies or antibody fragments by expressing a nucleic acid encoding the antibody or antibody fragment in an appropriate host cell. Non-limiting examples of recombinant antibody expression and selection techniques, inclusive of phage display methods, are provided in Chapter 17 of Coligan et al., CURRENT PROTOCOLS IN IMMUNOLOGY and Zuberbuhler et al., 2009, Protein Engineering, Design & Selection 22 169.

As used herein, the term "MAPK inhibitor" refers to any compound or chemical entity that, upon administration to a subject, results in inhibition the MAPK pathway in one or more cells, such as cancer cells, of the subject. MAPK inhibitors include but are not limited to low molecular weight inhibitors, antibodies or antibody fragments, antisense constructs, small inhibitory RNAs (i.e. RNA interference by dsRNA; RNAi), and ribozymes. In some embodiments, the MAPK inhibitor is a small organic molecule. MAPK inhibitors include, for example, RAS inhibitors, RAF inhibitors, MEK inhibitors, ERK inhibitors, JNK inhibitors and/or p38 inhibitors.

The MAPK pathway inhibitor may be any as are known in the art, inclusive of specific inhibitors of Ras (i.e., HRas, KRas and/or NRas), Raf (i.e., A-Raf, B-Raf and/or C-Raf), mitogen-activated protein kinase kinase (i.e., MEK1/2) and/or extracellular signal-regulated kinase (i.e., ERK1/2) function and/or signalling, inclusive of mutant variants thereof. By way of example, such MAPK pathway inhibitors may be chosen from among:

i) MEK inhibitors: AZD6244, R04987655, R05126766, TAK-733, MSC1936369B (AS703026), GSK1 120212, BAY86-9766, GDC-0973, GDC-0623, PD325901, ARRY-438162, CM 040, E6201, ARRY300;

ii) Raf and/or BRaf selective inhibitors: PLX4032, GSK21 18436, Sorafenib (BAY-43-9006), BMS-908662 (XL-281), RAF265, RG-7256 (R05212054, PLX3603), R05126766, ARQ-736, E-3810, DCC-2036;

iii) ERK inhibitors: Ulixertinib (BVD-523), SCH772984, DEL-22379, MK-8353 (SCH900353), AZD0364, VX-Ile, CC-90003;

iv) Ras inhibitors: MCI-062, Salirasib, BAY 293, ARS-1620.

It is envisaged that the BET inhibitor may be any as is known in the art. As used herein, the term "BET inhibitor" refers to a compound that binds to BET and inhibits and/or reduces a biological activity of BET. In some embodiments, the BET inhibitor substantially or completely inhibits a biological activity of BET. In some embodiments, the biological activity is binding of BET to chromatin (e.g., histones associated with DNA) and/or another acetylated protein. Suitably, the BET inhibitor inhibits one or more of BRD2, BRD3, BRD4, and BRDT. BET inhibitors include modulators of bromodomain-containing proteins such as the benzimidazole derivatives disclosed in U.S. Pub. No.: 2014/0336190. Exemplary BET inhibitors include I-BET 151 (GSK1210151A), I-BET 762 (GSK525762), OTX-015, TEN-010, CPI-203, CPI-0610, olinone, RVX-208, LY294002, AZD5153, MT-1 and MS645.

In another aspect, the invention relates to a method of treating or preventing an EBV-associated disease, disorder or condition in a subject, said method including the steps of:

(a) administering to the subject a population of allogeneic T cells that bind or recognize an epitope of an EBV antigen; and (b) administering to the subject a therapeutic agent, wherein the therapeutic agent is selected from the group consisting of an immunotherapeutic agent, a MAPK pathway inhibitor, a BET inhibitor and any combination thereof;

to thereby treat or prevent the EBV-associated disease, disorder or condition in the subject.

In a related aspect, the invention resides in a pharmaceutical composition for treating or preventing an EBV-associated disease, disorder or condition in a subject, the composition comprising:

a population of allogeneic T cells that bind or recognize an epitope of an EBV antigen;

a therapeutic agent, wherein the therapeutic agent is selected from the group consisting of an immunotherapeutic agent, a MAPK pathway inhibitor, a BET inhibitor and any combination thereof; and optionally a pharmaceutically acceptable carrier, diluent and/or excipient.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The statements which follow apply equally to the two aforementioned aspects.

Suitably, the population of allogeneic T cells and cells of the EBV-associated disease, disorder or condition share a human leukocyte antigen (HLA) allele that encodes a MHC protein. In particular embodiments, the MHC protein presents the epitope of the EBV antigen on cells of the EBV-associated disease, disorder or condition.

The immunotherapeutic agent, the MAPK pathway inhibitor and/or the BET inhibitor can be any as are known in the art, such as those hereinbefore described. In particular embodiments, the MAPK pathway inhibitor is or comprises a MEK1/2 inhibitor. In another embodiment, the immunotherapeutic agent is or comprises an immune checkpoint inhibitor, such as an anti-PD1 antibody.

Suitably, the population of allogeneic T cells is administered prior to, simultaneously with and/or subsequent to administration of the therapeutic agent. Accordingly, in certain embodiments, the subject is administered the therapeutic agent and subsequently administered the allogeneic T cells. In alternative embodiments, the individual is administered the allogeneic T cells and subsequently administered the therapeutic agent. In a further alternative embodiment, the allogeneic T cells are administered simultaneously with the therapeutic agent.

In one embodiment, the method of the present aspect further includes the initial step of generating the population of allogeneic T cells in vitro, such as by those methods hereinbefore described.

Suitably, the EBV antigen and/or the further EBV antigen is selected from the group consisting of EBNA1, EBNA2, EBNA3A, EBNA3B, EBNA3C, LMP1, LMP2 and any combination thereof. More particularly, the EBV antigen and/or the further EBV antigen suitably is or comprises EBNA1, LMP1 and/or LMP2.

Suitably, the EBV-associated disease, disorder or condition is or comprises an EBV-associated cancer, such as those hereinbefore described. In one embodiment, the EBV-associated cancer is selected from the group consisting of nasopharyngeal carcinoma, NKT cell lymphoma, Hodgkin's Lymphoma, post-transplant lymphoproliferative disease, Burkitt's lymphoma, Diffuse large B-cell lymphoma, gastric cancer, and any combination thereof.

In still another aspect, the invention relates to use of a first population of allogeneic T cells, such as those described herein, that bind or recognize a first epitope of an EBV antigen in the manufacture of a medicament for the treatment or prevention of an EBV-associated disease, disorder or condition in a subject; wherein the first population of allogeneic T cells is to be administered in combination with: (a) a second population of allogeneic T cells, such as those described herein, that bind or recognize a second epitope of the EBV antigen or a further EBV antigen; and/or (b) a therapeutic agent, such as that described herein, wherein the therapeutic agent is selected from the group consisting of an immunotherapeutic agent, a MAPK pathway inhibitor, a BET inhibitor and any combination thereof.

In a final aspect, the invention provides a first population of allogeneic T cells, such as those described herein, that bind or recognize a first epitope of an EBV antigen for use in the treatment or prevention of an EBV-associated disease, disorder or condition in a subject; wherein the first population of allogeneic T cells is to be administered in combination with: (a) a second population of allogeneic T cells, such as those described herein, that bind or recognize a second epitope of the EBV antigen or a further EBV antigen; and/or (b) a therapeutic agent, such as that described herein, wherein the therapeutic agent is selected from the group consisting of an immunotherapeutic agent, a MAPK pathway inhibitor, a BET inhibitor and any combination thereof.

With respect to the aforementioned aspects, the term "subject" includes but is not limited to mammals inclusive of humans, performance animals (such as horses, camels, greyhounds), livestock (such as cows, sheep, horses) and companion animals (such as cats and dogs). In one particular embodiment, the subject is a human.

So that preferred embodiments may be described in detail and put into practical effect, reference is made to the following non-limiting Examples.

EXAMPLES

Example 1

Allogeneic "off-the-shelf" T cell therapy has emerged as a powerful tool to treat infectious complications in transplant recipients. These allogenic antigen-specific T cells are expanded from peripheral blood lymphocytes collected from a large panel of healthy donors provides diverse HLA coverage and can be cryopreserved and administered in HLA-matched transplant patients in need. In this Example, we provide the preclinical assessment of allogeneic EBV-specific T cells as a therapeutic tool for the treatment of multiple cancers. Furthermore, we have also demonstrated that a combination of allogeneic antigen-specific T cells and antibodies blocking the PD1/PD-L1 axis significantly improved the efficacy of adoptive T cell therapy against EBV cancers.

Materials & Methods

Cell Culture

The EBV-associated cell lines used in this study were purchased from the American Type Culture Collection (ATCC, Manassas, Virginia, USA) and were cultured and maintained as per ATCC recommendations. The respective EBV-associated cell lines used in the study and their respective HLA is listed in Table 1. The cultures of these cell lines were maintained by incubating at 37° C. with 20% oxygen levels and 5% $CO_2$. All tissue culture plasticwares was purchased from Corning® Stone Staffordshire, UK (flasks and plates) and Costar® Washington DC, USA (plastic pipettes). All the cell lines were regularly tested for *Mycoplasma* infection and authenticated using short tandem repeat (STR) profiling by scientific services at QIMR Berghofer Medical Research Institute.

RNA Extraction and Quantitative Real-Time PCR

RNA was extracted either from respective cell lines using the QIAgen RNeasy® kit (Valencia, CA, USA) as per manufacturer's directives. $1\times10^6$ cells of respective cell lines were plated and harvested using trypsin-EDTA (Sigma Aldrich®) and washed (PBS, 2 times) after which appropriate volume of RLT buffer at 4° C. (supplied in the kit) was added and following steps as indicated by manufacturer was performed. A DNAse digestion step was performed using the DNAse enzyme provided in the iScript™ cDNA kit (Bio-Rad Laboratories Inc) after RNA extraction. The RNA quality and quantity was accessed using Nanodrop ND-1000 spectrophotometer (Thermo-Scientific). Reverse transcription was performed using iScript™ Reverse Transcriptase (Bio-Rad Laboratories Inc.) as per manufacturer instruction. The cycle condition used was: Priming at 25° C. for 5 minutes, reverse transcription at 46° C. for 20 minutes and reverse transcriptase inactivation at 95° C. for 1 minute. qRT-PCR was performed in 384 well plate using Biorad CFX384 Touch™ Real-Time PCR Detection System. The primers comprised of EBV-associated genes LMP1, LMP2 and EBNA1 that were obtained from the respective publications. The composition of the mastermix in an overall volume of 10 μL include: 5 μL of Sybr green, 1 mM of each primers, 1 μL of diluted cDNA and 3 μL of $H_2O$ for three biological replicates performed in duplicates. The cycle condition used was: 95° C. for 5 minutes, followed by 40 cycles of the following: 95° C. for 10 seconds, 60° C. for 10 seconds and 72° C. for 5 seconds, and a final elongation step of 72° C. for 5 minutes. Calculations of $C_t$ value was performed using the accompanying Biorad CFX384 software, version 1.5.0.39 following which the calculations were performed using the $\Delta\Delta C_t$ method, with values normalized to 18sRNA and HPRT. For each biological cDNA sample analysis, a negative control containing cDNA solution without treating with reverse transcriptase to ensure no genomic DNA contamination. Alongside, a regular negative control containing only $H_2O$ was included for each primer set. The primers comprised of LMP1: FP-5'-CAGTCAGGCAAGCCTATGA3', RP-5'CTGGTTCCGGTGGAGATGA3'; LMP2: 5'-AGCTGTAACTGTGGTTTCCATGAC-3', RP-5'-GCCCCCTGGCGAAGAG-3'; EBNA1: FP-5'-TA-CAGGACCTGGAAATGGCC-3', RP-5'-TCTTT-GAGGTCCACTGCCG-3'; HPRT1: FP-5'-CCTGGCGTCGTGATTAGTGAT-3', RP-5'-

AGACGTTCAGTCCTGTCCATAA-3'; 18sRNA: 5'-CGAAAGCATTTACCAAGGAC-3', RP-5'-TTATTGTGTCTGGACCTGG-3'.

Generation of T Cells

To generate LMP/EBNA1-specific "off the shelf" T-cell bank, peripheral blood mononuclear cells (PBMCs) were harvested from 100-300 mL of venous blood of seropositive donors covering a wide HLA spectrum. The AdE1-LMPpoly vector which comprised of a polyepitope of 16 HLA-restricted LMP1&2 epitopes fused to a truncated gly/ala deleted EBNA1 gene [11, 12], was then used to infect 30% of the PBMCs (MOI of 10:1). These transfected PBMCs were then irradiated and co-cultured with the remaining PBMCs for two weeks. Cultures were supplemented with fresh growth medium and 120 IU/mL of recombinant IL-2 every 3-4 days (Komtur Pharmaceuticals). Expanded T-cells were tested for antigen specificity and microbial contamination prior to release for infusion. The respective T cells used to target the HLA-matched EBV-associated cancer cell lines are listed in Table 1.

Intracellular Cytokine Assay

To analyse the frequency of LMP1&2- and EBNA1-specificity in the AdE1-LMPpoly transfected T-cells products, they were stimulated for 4 hours in the presence of GolgiPlug (BD Biosciences) with a pool of defined epitopes from LMP1&2 or EBNA1 or with an overlapping set of peptides encompassing the whole EBNA1 protein (all from Mimotopes, GenScript or JPT Technologies). For multiparametric analysis, cells were stimulated for 4 hours in the presence of GolgiPlug and GolgiStop (BD Biosciences) with the peptides listed above and anti-CD107a-FITC (BD Biosciences). Cells were then washed and stained with anti-CD8-PerCPCy5.5 (eBioscience) and anti-CD4-PECy7 (BD Biosciences), fixed and permeabilised with Cytofix/Cytoperm (BD Biosciences), washed again and stained with anti-IFN-γ-AF700 (all from BD Biosciences) [11]. After a further wash, cells were resuspended in PBS and acquired using a BD LSR Fortessa with FACSDiva software (BD Biosciences). Post-acquisition and Boolean analysis was performed using FlowJo software (TreeStar).

Cell Viability Assay

Cell viability assay was performed using the CellTiter 96@AQueous one cell viability assay reagent (Promega, WI, USA) for three biological replicates per EBV-associated cancer cell lines in triplicate. Briefly, the cancer cells (target cells) were plated at a density of 5000 cells per well in an overall media volume of 200 μL on a 96-well tissue-culture plate (BD Falcon™). The effector AdE1-LMPpoly transfected T cells were freshly thawed in RPMI-1640 with 10% FCS and 120 IU/mL of recombinant IL-2 at 37° C. and 50% $CO_2$. Post 24 hrs of plating and incubation at 37° C. and 50% $CO_2$, the effector T cells were mixed to the target cells at a gradient ratio of effector to target (E:T) of 5:1-100:1. The exact number of T cells (To) used per E:T ratio ($E_T$) was independently used as control alongside PBS treated target cells ($E_s$) and sole media ($M_0$). After 24 hrs of incubation at 37° C. and 50% $CO_2$, MTS was added to each well (1:100 dilution in media) and was incubated for 1 hour following which the plate was centrifuged at 1,200×g at room temperature for 5 min and absorbance of the mixture at an optical density of 490 nm was measured via a microplate reader. The relative cell viability was calculated using the following formula:

$$\text{Relative cell viability} = \frac{(E_T - M_0) - (T_O - M_0)}{(E_S - M_0)}$$

Cell Cytotoxicity Assay

Cell cytotoxicity assay was performed using the CytoTox 96® Nonradioactive Cytotoxic Assay Kit (Promega, WI, USA) for three biological replicates per EBV-associated cancer cell lines in triplicate [14]. Briefly, the cancer cells (target cells) were plated at a density of 5000 cells per well in an overall media volume of 200 μL on a 96-well tissue-culture plate and similar condition to that of cell viability assay was maintained as described previously. Alongside, we also seeded exact number of target cells ($E_M$). Following 24 hrs of mixing the effector and target cells at 37° C., 10× lysis agent was added to the $E_M$ well and incubated at 37° C. and 50% $CO_2$ for 45 min. Following complete lysis of target cells, the plate was centrifuged at 1,200×g at room temperature for 5 min, and the 50 μl supernatant of each well was transferred to another plate. Assay buffer was mixed with substrate mix and aliquoted to each well. Following termination with stop solution, the absorbance of the mixture at an optical density of 490 nm was measured via a microplate reader. The relative lysis in experimental and control well was calculated as follows:

$$\text{Relative cytotoxicity} = \frac{(E_T - M_0) - (T_O - M_0)}{(E_T - M_0) - (E_S - M_0)}$$

Polychromatic Profiling of Cancer-Cell Phenotype

The respected EBV-associated cancer cells were plated at a density of $1\times10^5$ cells per well and after 24 hours, were mixed with T cells with an effector to target (E:T) of 50:1 and incubated for 24 hr 37° C. and 50% $CO_2$. For assessing the impact of T cells on cancer cells, cells were then incubated at 4° C. with the following antibody: human anti-CD45-V500, anti-CD3-AF700, anti-Ki67-BV421, anti-BCL2-FITC and anti-Active Caspase 3-BV605. Cells were acquired using a BD LSR Fortessa with FACSDiva software (BD Biosciences) and post-acquisition analysis was performed using FlowJo software (TreeStar).

Polychromatic Profiling of AdE1-LMPpoly Transfected T-Cell Phenotype

The effector AdE1-LMPpoly transfected T cells were freshly thawed and were mixed to the target cells ($1\times10^5$) at an effector to target (E:T) of 50:1 and incubated for 24 hr 37° C. and 50% $CO_2$. For assessment of surface phenotype, cells were then incubated at 4° C. with the following antibody panels: (i) human anti-CD45-V500, anti-CD3-AF700, anti-CD4-PECy7 and anti-CD8-PerCPCy5.5; (ii) human anti-CD45-V450, anti-CD4-AF700, anti-CD8-PerCPCy5.5, anti-CD14-eFluor450, anti-CD19-eFluor450; anti-PD-1-BV786; (iii) MHC-Class I antibody (clone W6/32) (home made, raised in mouse), LIVE/DEAD Fixable Near-IR Dead Cell Stain (Thermo Fisher Scientific, MA). For intracellular analysis, cells were treated with TF Fixation/Permeabilization buffer (BD Biosciences) and then stained in the presence Perm/Wash with the following antibodies: (i) anti-perforin-BV421, anti-granzyme B-AF700 and anti-granzyme K-FITC. Cells were acquired using a BD LSR Fortessa with FACSDiva software (BD Biosciences) and post-acquisition analysis was performed using FlowJo software (TreeStar).

Animal Housing

All animal work was approved by the QIMR Berghofer Medical Research Institute, Animal Ethics Committee (number A0707-606M) and was performed in strict accordance with the Australian code for the care and use of animals for scientific purposes. All experimental animals were maintained on a mixed (129SV/E X C57BL/6) strain and were housed at the Queensland Institute of Medical Research Animal Facility in OptiMICE® caging (Centennial, Colorado, USA) on a 12-hour light-dark cycle at 25° C. Dried granule food was sterilized by radiation irradiation. The mice had free access to the food and sterile water.

In Vivo Assessment of Therapeutic Efficacy of Allogeneic EBV-Specific T-Cells

A total of 12-24 female NOD/SCID mice (depending on the experiment) of 7-8 weeks old were used in this study. The mice were subjected to irradiation with 0.8 Gy cobalt-60 and after 4 hours, were subcutaneously injected with $5\times10^6$ cells of respective EBV-associated cancer cells with a 29-gauge needle. The mice were monitored for tumour growth, weight and body score thrice weekly. Once the tumour was palpable, the mice were randomised into respective groups and were treated with respective dosage of PBS or $20\times10^6$ tumour HLA matched allogenic EBV-specific T-cells. The tumour size in these mice were measured thrice weekly using the Vernier Calipers. To calculate tumour area the following formula was used: tumour area=B*S where B=largest tumour measurement and S=the smallest, based on two-dimensional caliper measurements as previously described [13].

In Vivo Assessment of Therapeutic Efficacy of Allogeneic EBV-Specific T-Cells in Humanized Mice Model Fresh human $CD34^+$ cord blood cells were obtained from healthy full-term newborns after written parental consent and were enriched using immunomagnetic beads according to the manufacturer's instructions ($CD34^+$ selection kit, Miltenyi Biotec, Bergisch-Gladbach, Germany). Female NRG mice of 7-8 weeks old were irradiated twice with 275 cGy at 3-4 hours apart following which they were intravenously injected with $5\times10^4$ CD34+ cells (HLA matched to AdE1-LMPpoly transfected T-cells used for treatment) per mouse with a 29-gauge needle. The mice were monitored twice weekly for body weight, body score and adverse reactions including graft versus host disease (GVHD). In addition, tail vein bleeds were performed at weeks 4, 8, 10 and 12 during which 100 μL to 200 μL of blood was collected into EDTA tubes from each mouse at a time to monitor the reconstitution of the human immune system. To assess the reconstitution from the human CD34+ cord blood cells, the surface phenotyping was performed using human anti-CD45-V500, mouse anti-CD45-V450, anti-CD3-APC, anti-CD4-AF700, anti-CD8-PerCPCy5.5, anti-CD8-PerCPCy5.5, anti-CD14-FITC, anti-CD19-PeCy5, anti-CD23-BV786, and anti-CD56-BV650. At the $12^{th}$ week of reconstitution, the humanised NRG mice were intravenously injected with EBV B95-8 at a dose of $10^6$ EBV particles in 100 μL PBS under non-anaesthetic conditions using a 29-gauge needle. At $13^{th}$ day post EBV infection, the mice were treated with respective dosage of PBS or $20\times10^6$ tumour HLA matched or switched AdE1-LMPpoly transfected T-cells. The HLA of the respective cord blood cells and the corresponding T cells used to treat the lymphoid malignancies are listed in Table 1. The mice were monitored for 14 days post T cells treatment following which were culled and their spleens were analysed tumour burden.

Immunohistochemistry

For histologic examination tissues were collected and fixed in 4% formaldehyde in PBS after washing (PBS, 3 times) and was stored in 70% ethanol prior to processing. The tissues were then embedded in paraffin blocks, and 5-μm-thick sections prepared for staining. Tissues were embedded in paraffin and 4 μm sections mounted onto Superfrost plus slides using the Sakura Tissue-Tek® TEC™ (Sakura Finetek, Tokyo, Japan). Immunohistochemistry was performed in assistance with the QIMR Berghofer Medical Research Institute in-build facility. Antigen retrieval was performed using 2.94 g tri-sodium citrate in 1 L MQ (pH 6.0) buffer and microwaved. Tissue sections were permeabilized in 0.2% Triton X-100/PBS for 5 min, followed by 0.05% Triton X-100/PBS for 10 min. Tissue sections were treated with 3% (vol/vol) $H_2O_2$ before immunostaining using the anti-CD3 (1:40 Dako M7254) antibody in 2% BSA followed by secondary antibody (VEMP7402) Dako EnVision™ (Agilent, system Waukesha, WI, USA) and counterstaining with haematoxylin. The slides were scanned on the Aperio® Scanscope® XT (Aperio®, Vista, USA) using 20× or 40× objecting.

Gene Signature Profile Using NanoString and Infiltrate Profiling

A total of 6 female NOD/SCID mice of 8 weeks old were irradiated with 0.8 Gy cobalt-60 and after 4 hours, were subcutaneously injected with $5\times10^6$ cells of SNU719 with a 29-gauge needle. Once the tumour size reached 40 $mm^2$, the mice were treated with $20\times10^6$ TI_001 T cells. After 5 days, the tumours were harvested and using FACS, the T cells sorted for viable $CD8^+$ population using human anti-CD45-V500, mouse anti-CD45-V450, anti-CD3-APC, anti-CD4-PE and anti-CD8-PerCPCy5.5. RNA was isolated from the sorted viable $CD8^+$ population of individual mice using a Qiagen RNAeasy kit as described above. Gene expression analysis was performed using the customized 326-NanoString Immune gene expression panel. 50 ng of total RNA per mice sample was used in a final volume of 5 μl and was mixed with a 3' biotinylated capture probe alongside a 5' reporter probe tagged with a fluorescent barcode from the custom gene expression code set. Probes and target transcripts were hybridized at 65° C. for 12-16 h. Hybridized samples were run on the NanoString nCounter preparation station using the recommended manufacturer protocol, in which excess capture and reporter probes were removed and transcript-specific ternary complexes were immobilized on a streptavidin-coated cartridge. The samples were scanned at maximum scan resolution on the nCounter Digital Analyzer. Data were processed using nSolver Analysis Software and the nCounter Advanced Analysis module. For gene expression analysis data were normalized using the geometric mean of housekeeping genes selected by the GeNorm algorithm.

Statistical Analysis

Student's t-test or one-way or two-way ANOVA with Bonferoni post hoc or Mann-Whitney U test testing (specified in figure legend) was performed using GRAPHPAD PRISM v6.0 (GraphPAd Software, LaJolla, CA, USA) and the p-values were calculated as indicated in figure legends. Asterisks indicate significant difference (*$p<0.05$, $p<0.01$, *$p<0.001$ and ****$p<0.0001$), ns=not significant.

Results

In Vitro Recognition of Multiple Cancers by Allogenic "Off-the-Shelf" EBV Specific T-Cells To assess the expression of EBV-encoded genes (LMP1, LMP2 and EBNA1) in multiple EBV-associated malignancies including NPC, gastric cancer, NKT lymphoma and BLCLs, we employed qRT-PCR and analyzed the transcript levels for each of these genes. We observed that in all EBV-associated malignancies, LMP2 and EBNA1 was consistently expressed at higher level when compared to LMP1 (FIG. 1A). We assessed susceptibility of these EBV-positive cancer cells to allogenic "off-the-shelf" EBV-specific T cells specific for LMP1, LMP2 and/or EBNA1 (FIG. 1B; Table 2). Data presented in FIG. 1C-D shows that gastric cancer (SNU719), NPC (C17 and C661) and NKT lymphoma (SNKT16) cells were efficiently recognized by allogenic HLA matched EBV-specific T cells at varying effector to target ratios. Furthermore, Annexin V binding assay also showed increase in Annexin V binding capacity indicating target cell death in comparison to the mock-treated control (FIG. 1D-E).

Figure 2:
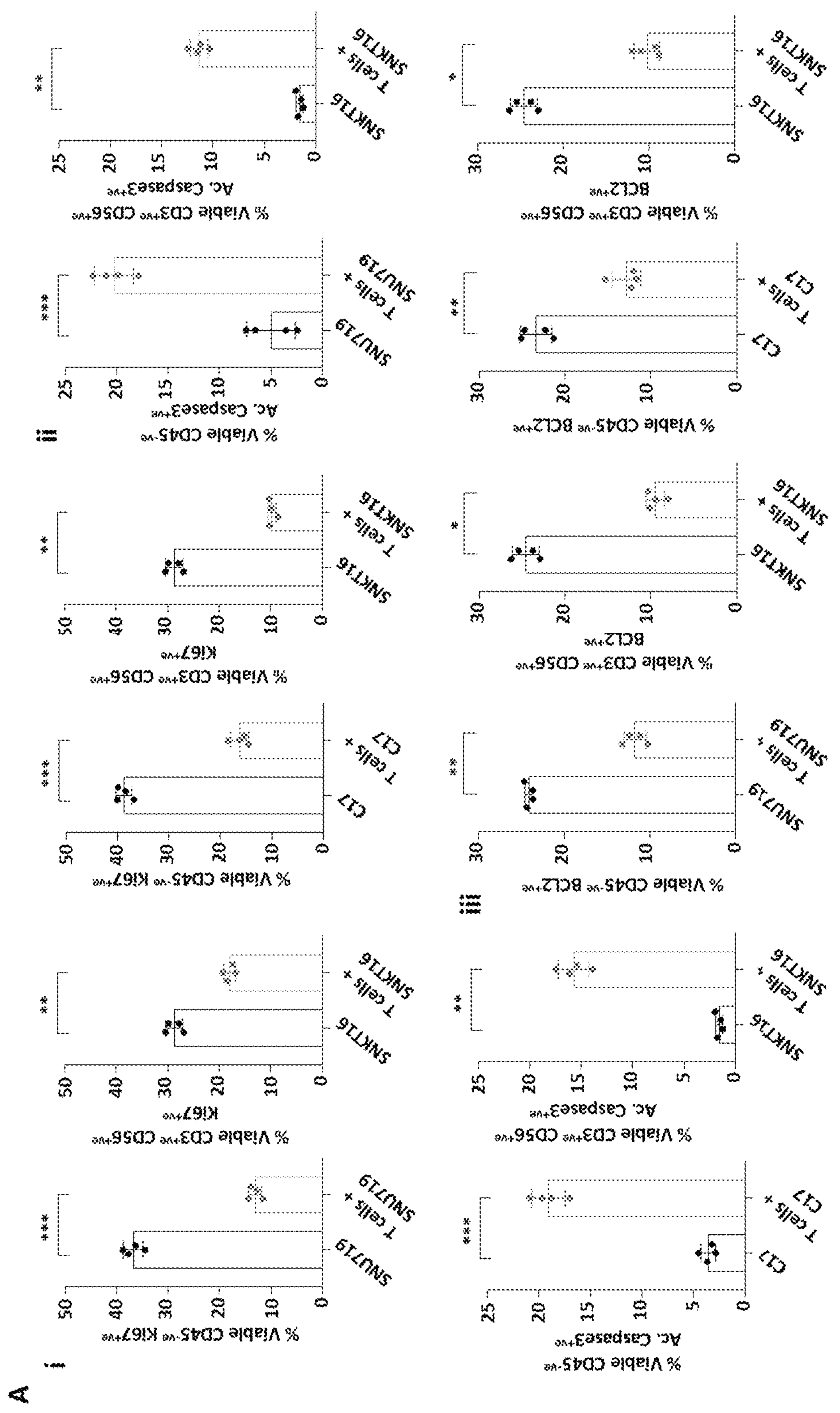
FIG. 2: Phenotyping the characteristics of the EBV-associated cancer cells effector T cells in vitro. (A) Statistical representation comparing the (i) percentage of Ki67+ population; (ii) percentage of active Caspase 3+ population; and (iii) percentage of BCL2+ population of viable indicated EBV-associated cancer cell lines after 24 hours of mock (PBS) and HLA-matched T cells treatment. SNU719 and C17 were treated with TI_001 and TI_002 T cells respectively while SNKT16 was treated with both the T cells. Both SNU719 and C17 were gated as CD45-population while SNKT16 were gated as CD45+ CD3+ CD56+ population to distinguish out from the T cell population. (B) Statistical representation comparing the (i) percentage of CD8+ population; (ii) percentage of Ki67+ population; (iii) percentage of GnzB+ (Granzyme B) population; (iv) percentage of GnzK+ (Granzyme K) population; (iii) percentage of Perf+ (Perforin) population of viable T cells used to treat respective EBV-associated cancer cell lines as described in (A). Error bars represent the ±SEM from three independent experiments. P-values were calculated using one-way ANOVA: p<0.01, and *p<0.001.
Figure 2:
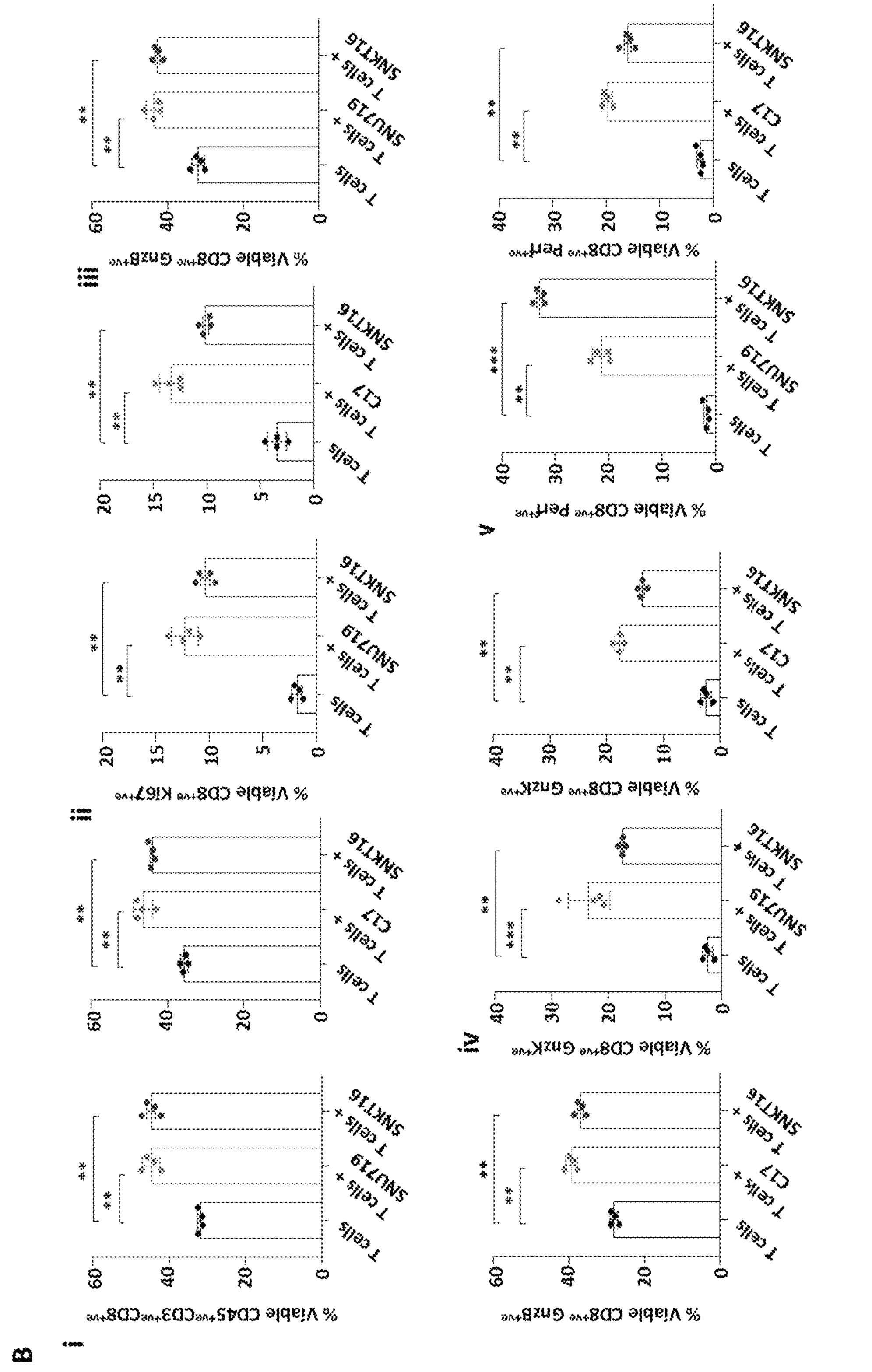

In the next set of experiments, we analysed the impact of the allogenic EBV-specific T cells on the phenotypic changes in EBV-associated cancer cells. We observed significant reduction ($p<0.001$) in proliferation rate of both gastric cancer, SNU719 and NPC, C17 cells, after 24 hrs in presence of HLA matched allogenic EBV-specific T cells as shown by Ki67staining (FIG. 2A). Furthermore, we also observed a significant increase ($p<0.001$) of active Caspase 3 staining in addition to significant reduction ($p<0.01$) in BCL2 staining suggesting increased cell death induced by the EBV-specific T cells (FIG. 2A). We also investigated the impact of EBV-associated cancer cells on allogenic EBV-specific T-cells. We observed a significant increase ($p<0.01$) in $CD8^+$ T cell population in presence of EBV-associated cancer cells (FIG. 2B). Consistent with this data, we observed a significant increase in Ki67 expression on $CD8^+$ T cells, when exposed to EBV-positive cancer cells (FIG. 2B). Furthermore, these T cells also showed a high level of effector function as indicated by significantly increased expression of GzmB, GzmK and Perf staining (FIG. 2B). Collectively, these data demonstrate that the allogenic EBV-specific T cells can efficiently recognize HLA-matched multiple types of EBV-associated cancer cells in vitro.

Figure 3:
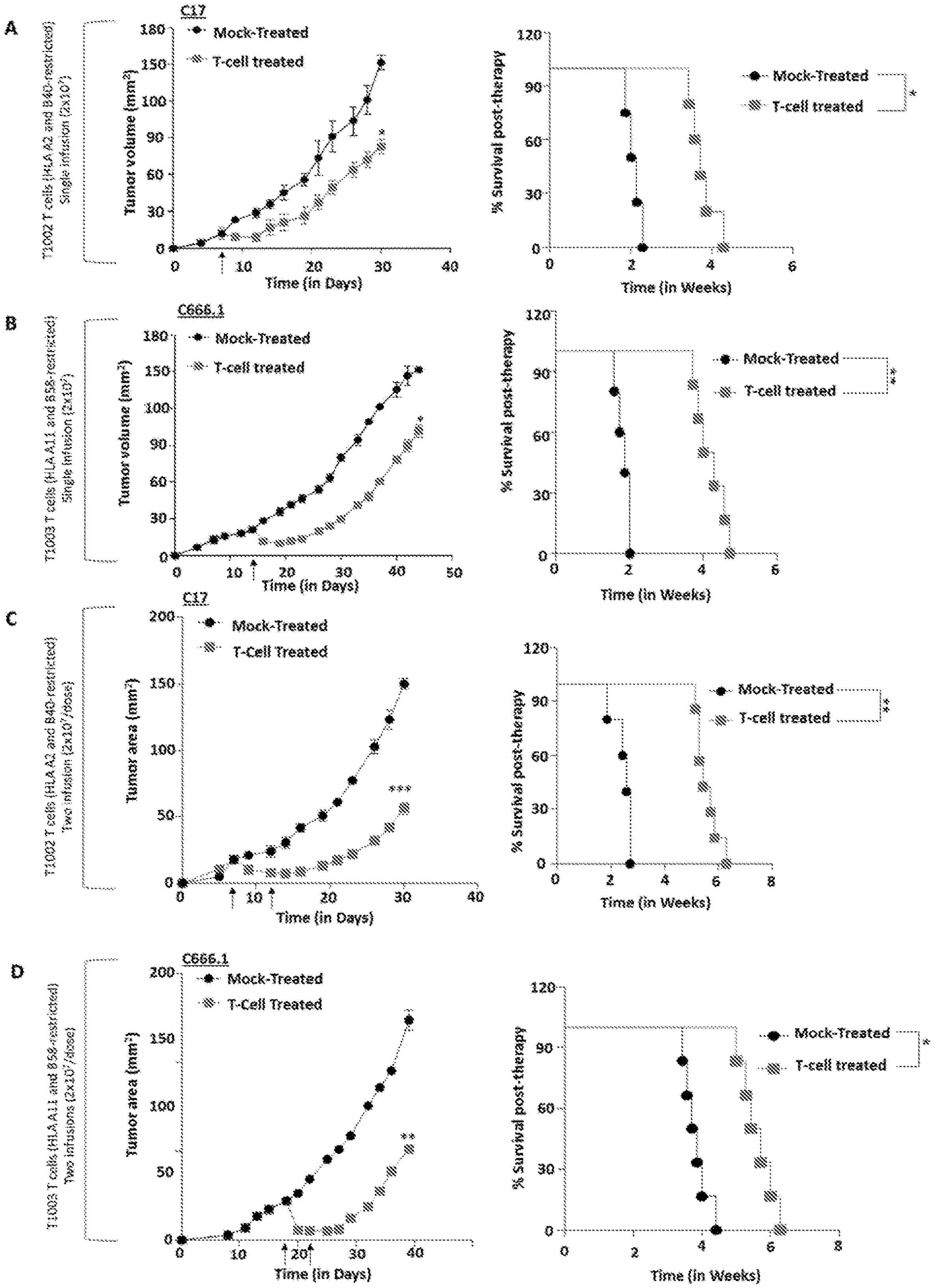
FIG. 3: Assessment of therapeutic efficacy of allogeneic EBV-specific cytotoxic T cells against solid cancers in vivo. Statistical representation of tumour growth and percent survival post T cell therapy observed after single dosage of T cells observed in (A) C17 and (B) C666.1 derived tumour xenografts; and double dosage of T cell therapy at an interval of 96 hours (indicated by the black arrows) in (C) C17 and (D) C666.1 derived tumour xenografts. C17 was treated with TI_002 while C666.1. treated with TI_004. Tumour size (area, mm2) was measured using a digital calliper and mean tumour size of each cohort was represented. The tumour growth of each cell line derived xenograft is represented as the mean tumour area ±SEM from n≥4 mice/group. The mice survival was monitored over the indicated period of time and the statistical significance of data was analysed by log-rank test: *p<0.05, p<0.01, and *p<0.001.

Assessment of Therapeutic Efficacy of Allogeneic EBV-Specific Cytotoxic T Cells In Vivo Having established efficient recognition of multiple EBV-associated cancers by allogenic EBV-specific T cells in vitro, we next assessed therapeutic efficacy of these effector cells in vivo. In the first set of experiments immuno-deficient NOD-SCID mice were inoculated with EBV-associated NPC tumours, C17 and C666.1 (subcutaneously) after irradiation. These animals were treated with HLA matched allogenic EBV-specific T cells when tumours of each animal reached 25 $mm^2$. These animals were treated with either a single or two infusions ($2\times10^7$ T cells for each infusion/animal) of allogeneic HLA matched EBV-specific T cells and monitored for tumour outgrowth. Data presented in FIG. 3 shows that a single infusion of allogeneic HLA A2/B40-restricted or HLA A11/B58-restricted LMP2-specific T cells ($2\times10^7$ T cells) were sufficient to significantly reduce the tumour outgrowth and also improved overall survival of tumour-bearing mice (FIGS. 3A & B). A further improvement in tumour burden and overall survival was observed when these animals were treated with two infusions of allogenic EBV-specific T cells (FIGS. 3C & D).

Figure 4:
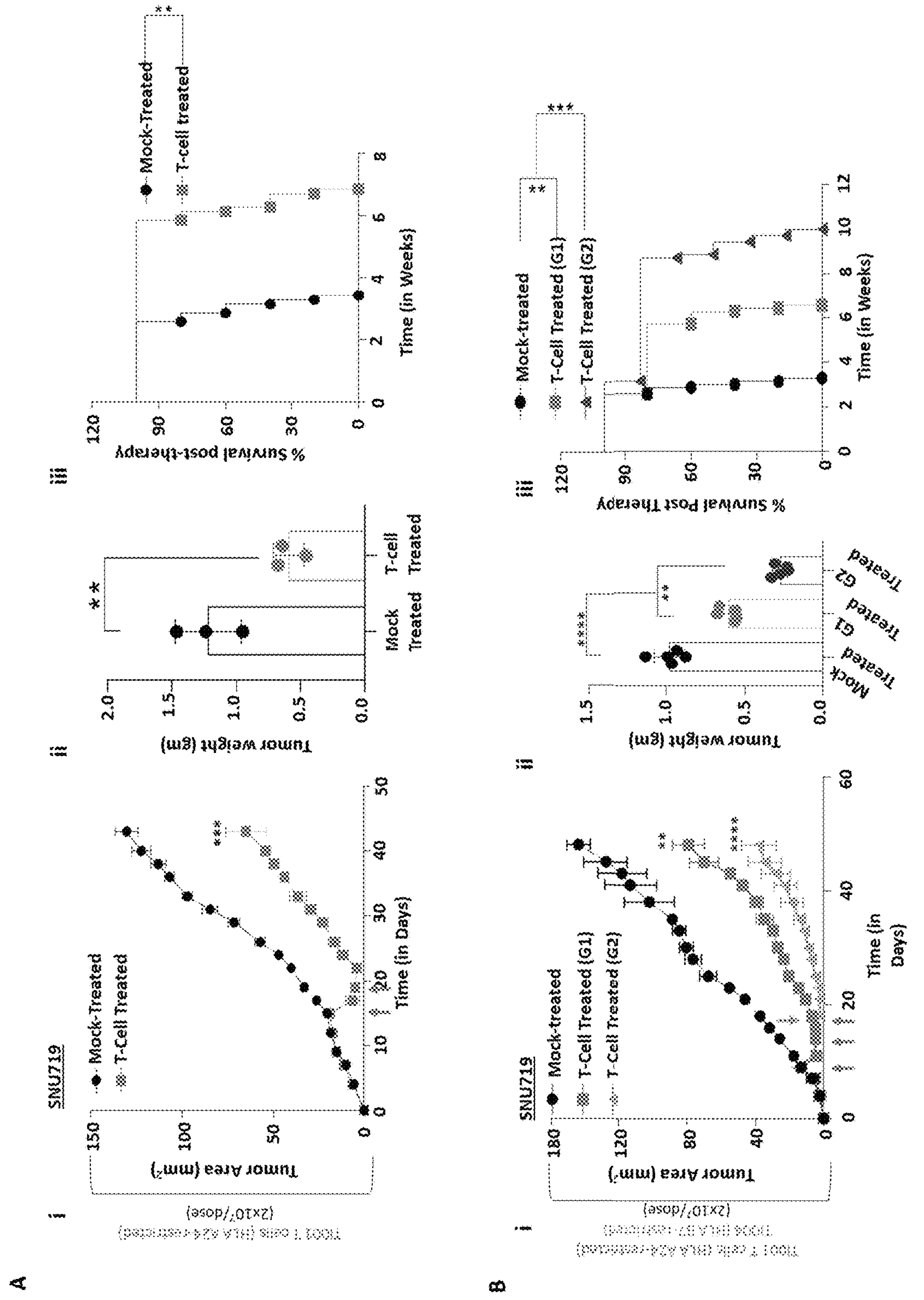
FIG. 4: Assessment of "switch antigen" therapy provides improved efficacy of the EBV-specific cytotoxic T cells in vivo. (A) Statistical representation of SNU719 derived xenograft indicating (i) tumour growth; (ii) tumour weight (in gms) at ethical limit of tumour growth; (iii) percent survival post T cell therapy observed in T cells treated (two dosage at an interval of 96 hours each) group compared to mock (PBS) treated control group. (B) Statistical representation of SNU719 derived xenograft indicating (i) tumour growth; (ii) tumour weight (in gms) at ethical limit of tumour growth; (iii) percent survival post T cell therapy observed in T cells treated (three dosage) group compared to mock (PBS) treated control group. The three arrows below the x axis indicate administration of three continuous dosage (at an interval of 96 hours each) of TI_001 while the single arrow indicates switching the third dose to TI_004, which was administered after two dosage of TI_001. The tumour growth of each cell line derived xenograft is represented as the mean tumour area ±SEM from n≥5 mice/group. The statistical significance of data of tumour weight was analysed by Mann-Whitney t-test. The mice survival was monitored over the indicated period of time and the statistical significance of data was analysed by log-rank test: p<0.01, *p<0.001, and ****p<0.0001.

In the next set of experiments, we extended the therapeutic efficacy analysis to gastric cancer. In these experiments, immuno-deficient NOD-SCID mice were inoculated with EBV-associated gastric cancer, SNU719 and treated with HLA A24-restricted allogenic LMP2-specific T cells when tumours of each animal reached 25 $mm^2$. Consistent with the data obtained with NPC tumour model, a significant reduction in tumour burden and improved overall survival was observed when these animals were treated with HLA matched allogenic LMP2-specific T cells (FIG. 4A). Interestingly, we noticed that while the tumour outgrowth was significantly reduced after first T cell infusion, this therapeutic benefit was less pronounced after second T cell infusion. A possible explanation for this phenomenon could be due to presence of immunosuppressive tumour microenvironment [16, 17] or HLA-loss leading immune escape [18], leading to adversely impact clinical outcome. Thus, we hypothesized that the EBV-associated tumours override the therapeutic impact of allogenic EBV-specific T-cells by altering their HLA-expression or modulating EBV gene expression which might hamper the presentation of EBV epitopes to the CD8+ T cells. To explore this hypothesis, we established three groups of mice bearing gastric cancer (SNU719) and treated one group of mice (G1) using three continuous dosage of the same HLA-matched allogenic EBV-specific T cells (HLA A24-restricted LMP2-specific T cells). Simultaneously, we also treated another group (G2) with two continuous dosage of the same HLA-A24-restricted allogenic EBV-specific T cells but switched the third dose to a different T cell line (HLA B7-restricted, EBNA1-specific) (FIG. 4B). We observed that, in comparison to G1, the G2 group demonstrated a significant reduction in tumour outgrowth and improved overall survival after the infusion of the third dosage of T cells (FIG. 4B). Interestingly, G1 group showed minimal impact on tumour growth after the third infusion and much higher tumour burden when compared to animals in G2 group (FIG. 4B). Collectively, these data clearly demonstrate that allogenic HLA matched T cells can efficiently block tumour outgrowth and improve overall survival of mice bearing EBV-associated epithelial tumours.

Figure 5:
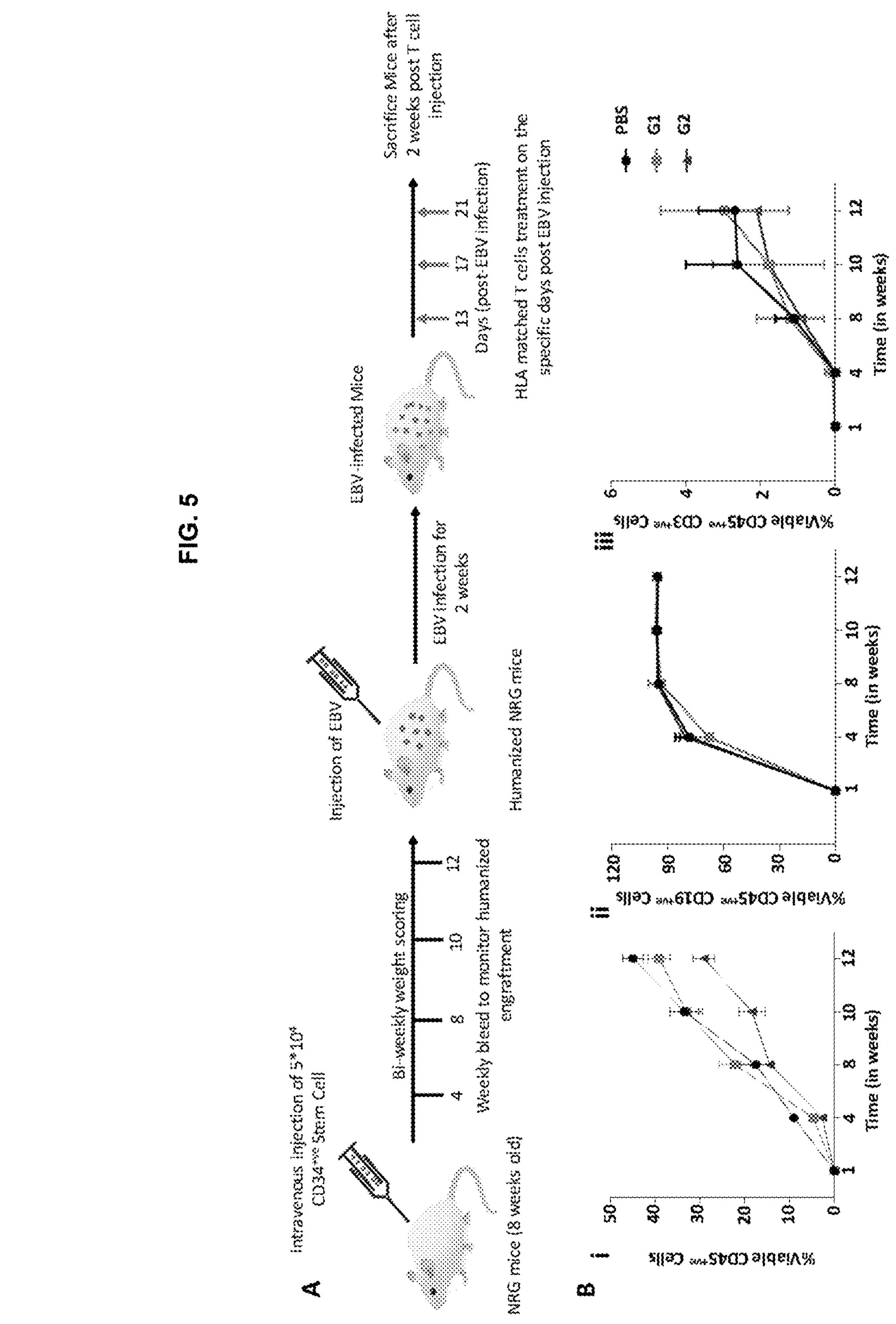
FIG. 5: Assessment of therapeutic efficacy of allogeneic EBV-specific cytotoxic T cells against lymphoid malignancies in vivo. (A) Schematic diagram demonstrating the reconstitution schedule of the human immune system over 12 weeks in NRG mice using CD34+ cells post irradiation and mice monitoring for graft versus host disease (GVHD). The schematics also illustrates the EBV virus was administered (QIMR-WIL strain), post-reconstitution and was monitored for 2 weeks for EBV incubation. HLA-matched T cells were administered on the indicated days (highlighted by the three arrows) post-EBV infection and the mice were sacrificed 2 weeks after T cell therapy. (B) Statistical representation highlighting the reconstitution of the human immune system over 12 weeks as indicated by presence of percentage of viable (i) CD45+; (ii) CD45+ CD3+; and (iii) CD45+ CD19+ population across respective groups. (C) Gross morphology of spleen illustrating the size and presence of lymphoid malignancies in the spleen of n=3 mice reconstituted with CB33A CD34+ cord blood cells across respective treatment groups. G1 represents administration of three continuous dosage (at an interval of 96 hours each) of TI_005 while G2 indicates switching the third dose to TI_002, which was administered after two dosage of TI_005. (D) Statistical representation comparing spleen weight (in gms) across respective treatment groups. (E) Gross morphology of spleen illustrating the size and presence of lymphoid malignancies in the spleen of n=3 mice reconstituted with CB03 CD34+ cord blood cells across respective treatment groups. G1 was treated with TI_002 while G2 was treated with TI_003 as per strategy indicated in (C). (F) Statistical representation comparing spleen weight (in gms) across respective treatment groups. The statistical significance of data of tumour weight was analysed by one-way ANOVA: p<0.01, and *p<0.001.
Figure 5:
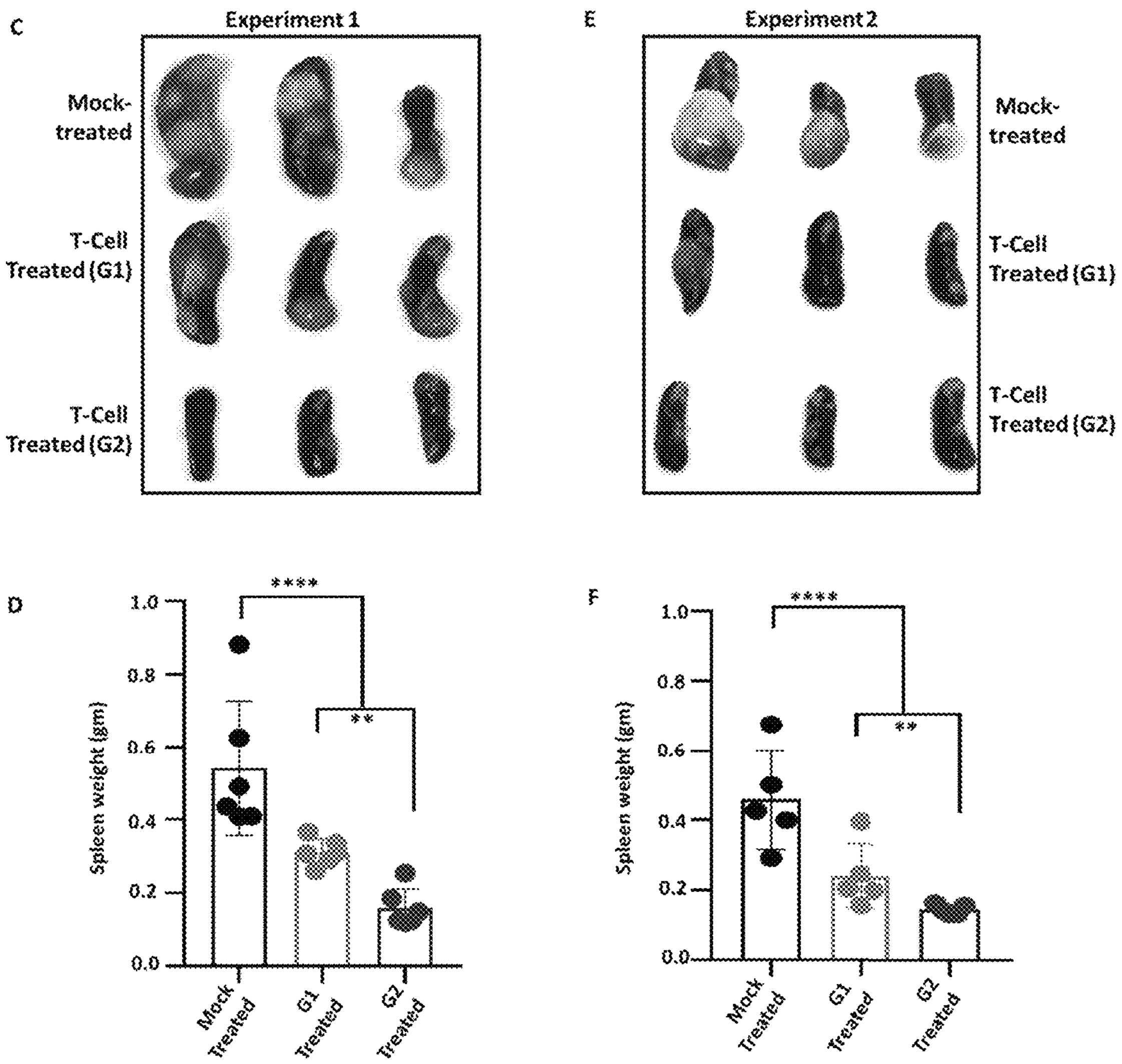

Allogeneic EBV-Specific T Cells Adoptive Immunotherapy Effectively Inhibits Outgrowth of EBV-Associated Lymphoid Malignancies As mentioned previously, EBV is etiologically involved with multiple diseases including lymphoproliferative diseases (LPD) in immunocompromised patients such as PTLDs, AIDs-associated lymphomas and other malignant lymphomas namely Hodgkin and Burkitt lymphoma [19-22]. To further demonstrate the potential therapeutic efficacy of allogenic EBV-specific T-cells, we utilized the humanized mice model harboring the functionally reconstituted human immune system. The reconstitution of human immune system was established using intravenous administration of cord blood derived $CD34^+$ stem cells in NOD-Rag1$^{null}$ IL2rg$^{null}$ (referred to as NRG) mice and these animals were regularly monitored as outlined in FIGS. 5A & B. After 12 weeks these mice were infected with EBV (QIMR-WIL strain) and following the development of EBV-LPD were adoptively treated with HLA-matched allogenic EBV-specific T cells. Two independent sets of experiments were performed. In the first set, EBV-LPD bearing NRG mice were split into three groups (6 mice in each group) and were either mock treated or infused with T cell therapy (referred to as G1 and G2). Animals in G1 group were treated with three doses of HLA A2 and A24-restricted allogeneic LMP1 and LMP2-specific T cells ($2\times10^7$ T cells/dose), while animals in G2 group were given two doses of HLA A2 and A24-restricted allogeneic LMP1 and LMP2-specific T cells ($2\times10^7$ T cells/dose) and a single dose of HLA A2, B40 and Cw3-restricted LMP1, LMP2 and EBNA1-specific T cells ($2\times10^7$ T cells). Data presented in FIG. 5C-D shows that animals in G1 group showed significantly reduced tumour burden when compared mock-treated mice. However, animals in G2 group treated with a combination of two different allogenic EBV-specific T cells showed significantly reduced tumour burden when compared to mock treated and G1 animals. These observations were further confirmed in a second set of independent experiments where animals treated with allogenic EBV-specific T cells also showed significantly lower tumour burden (FIG. 5E-F). These data further demonstrate that allogenic HLA matched EBV-specific T cells can efficiently block tumour outgrowth and improve overall survival of mice bearing EBV-associated lymphoid malignancies.

Figure 6:
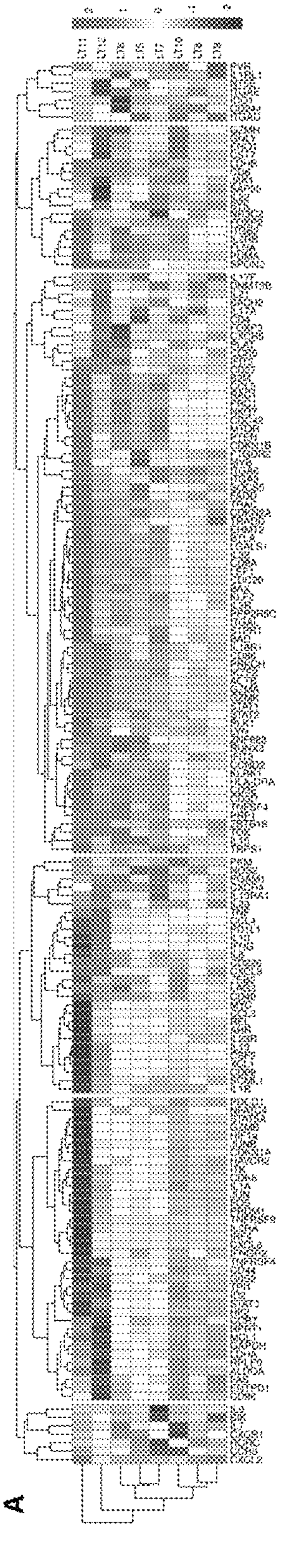
FIG. 6: Impact of PD1 inhibition on therapeutic efficacy of allogeneic EBV-specific cytotoxic T cells in vivo. (A) Heat-map representing gene signature of 326 genes observed RNA isolated from in the tumour infiltrating (TILs) CD8+ cells performed using NanoString Immune function panel. The TILS were isolated from SNU719 derived tumour xenograft from six independent mice (LT5-10) after 5 days post a single dose of TI_001 treatment when the tumour size reached 40 $mm^2$. The gene expression observed in TILS was compared to unstimulated (LT11) and EBV-pepmix stimulated (LT12). (B) Statistical representation comparing the (i) percentage of CD3+CD8+ population; (ii) percentage of CD8+PD1+ population; (iii) percentage of CD8+LAG3+ population; and (iv) percentage of CD8+ TIM3+ population of viable TILS (described in (A)) and compared to unstimulated T cells (T cell therapy). Error bars represent the ±SEM from three independent experiments. P-values were calculated using one-way ANOVA. Statistical representation of SNU719 derived xenograft indicating (C) tumour growth; (D) tumour weight (in gms) at ethical limit of tumour growth; (E) percent survival post T cell, anti-PD1 and combination of T cell and anti-PD1 therapy observed in respective treatment groups compared to mock (PBS) treated control group. The statistical significance of data of tumour weight was analysed by one-way ANOVA. The mice survival was monitored over the indicated period of time and the statistical significance of data was analysed by log-rank test: ns not significant, p<0.01, *p<0.001, and ****p<0.0001.
Figure 6:
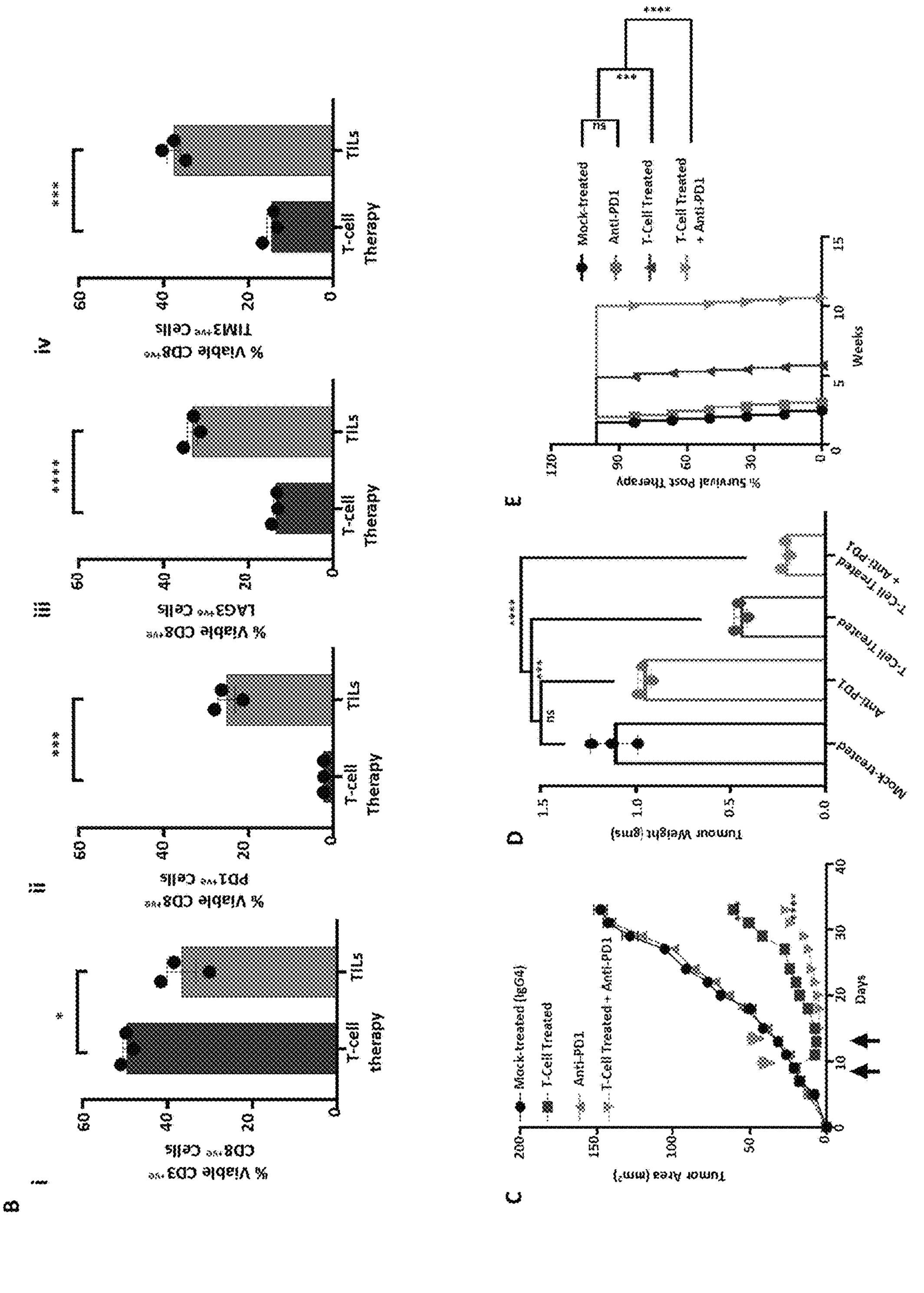

Blocking PD1/PD-L1 Axis Augments Therapeutic Efficacy of Allogeneic EBV-Specific T Cells To further delineate the interaction of adoptively transferred allogenic EBV-specific T cells and tumour cells in vivo, we isolated infiltrating T cells from the SNU719 tumours and analysed transcriptional signature using NanoString technology. In addition, we also validated expression of some of the checkpoint molecules using specific antibodies. Data presented in FIG. 6A shows heat map of gene expression in T cell therapy product and purified tumour infiltrating human T cells. This analysis showed that a number of cellular genes involved in effector cell function and transcriptional factors associated with effector function were down-regulated in tumour infiltrating human lymphocytes. In contrast, expression of a number of checkpoint molecules were upregulated in these T cells. To validate the expression of these checkpoint molecules, we stained tumour infiltrating human lymphocytes with specific antibodies and compared their expression with T cell therapy administered to tumour-bearing mice. This analysis confirmed the NanoString expression and showed that tumour infiltrating human lymphocytes expressed high levels of PD-1, LAG3 and TIM3 (FIG. 6B).

Based on these observations, we hypothesized that a combination of checkpoint inhibitor and T cell therapy may offer better therapeutic benefit against EBV-associated tumours. To test our hypothesis whether the upregulated PD1/PD-L1 axis influence the cancer cells in gaining adaptive immune resistance, we blocked PD1 using anti-PD1 antibody (Nivolumab) in combination with the allogenic EBV-specific T cell in vivo. Specifically, Nivolumab was administered 24 hrs after T cell infusion and we observed that the combination group demonstrated significantly reduced SNU719 gastric cancer outgrowth ($p<0.0001$) in comparison to monotherapy and mock-treated groups (FIG. 6C). In addition, we observed significantly reduced tumour size indicated by the reduced tumour weight observed in the combination group when compared to monotherapy groups (FIG. 6D). Importantly, we observed that the combination group demonstrated significantly improved ($p<0.0001$) survival post therapy in comparison to monotherapy or mock-treated group (FIG. 6E). Notably, the combination group showed ~2 fold ($p<0.01$) better survival in comparison to only T cell treated group (FIG. 6E). Collectively, these data highlight the PD1/PD-L1 signalling pathway negatively dictate the fate of the allogenic CD8+ T cells in eliminating the cancer cells as its inhibition enables augmentation of the allogenic EBV-specific CD8+ T cells in vivo.

TABLE 1

List of EBV-associated cancer cells and allogeneic EBV-specific T cells used to treat in the study

| Cancer cells or cord blood | HLA typing of cancer cells or cord blood | T cells used |
|---|---|---|
| SNU719 | A*24:02, 24:02;<br>B*07:02, 52:01;<br>C*07:02, 12:02 | TI_001 and TI_004 |
| C17 | A*02:01, 26:01;<br>B*44:02, 51:01;<br>C*05:01, 14:02 | TI_002 |
| C666.1 | B*58:02; C*03:04 | TI_003 |
| SNKT16 | A*02:01, 24:02;<br>B*48:01, 52:01; | TI_001 and TI_002 |

TABLE 1-continued

List of EBV-associated cancer cells and allogeneic EBV-specific T cells used to treat in the study

| Cancer cells or cord blood | HLA typing of cancer cells or cord blood | T cells used |
|---|---|---|
| | C*08:03, 12:02 | |
| CB33A | A*02:01, 03:01;<br>B*40:01, 44:02;<br>C*03:04, 05:01 | TI_005 and TI_002 |
| CBO3 | A*02:01, 03:01;<br>B*44:02, 58:01;<br>C*05:01, 07:18 | TI_001 and TI_003 |

TABLE 2

HLA and antigen recognition of the respective allogeneic EBV-specific T cells used in the study

| Allogenic EBV-specific T cells batch code | HLA typing of T cell donor | EBV antigen specificity (HLA restriction) |
|---|---|---|
| TI_001 | A*11:01, 24:02;<br>B*40:01, 40:01;<br>C*03:04, 03:04 | LMP2 (A*11:01, 24:02) and EBNA1 (C*03:04) |
| TI_002 | A*02:01, 02:01;<br>B*40:01, 40:01;<br>C*03:04, 03:04 | LMP1 (A*02:01); LMP2 (A*02:01, B*40:01); EBNA1 (*03:04) |
| TI_003 | A*11:01, 33:03;<br>B*40:01, 58:01;<br>C*03:02, 03:04 | LMP1 (58:01); LMP2 (B*40:01, 58:01) |
| TI_004 | A*03:01, 03:01;<br>B*07:02, 07:02;<br>C*07:01, 07:02 | EBNA1 (B*07:02) |
| TI_005 | A*02:01, 23:01;<br>B*41:02, 44:02;<br>C*05:01, 17:01 | LMP1 (A*02:01); LMP2 (A*02:01, 23:01) |

Example 2

Efficacy of Dual Combination of MEK1/2 and BET Inhibition with EBV-Specific T Cells Targeted therapies, which inhibit molecular or biochemical pathways critical for tumour growth and maintenance, could prove to be of great importance in making an impact on immune contexture of tumours. Of late, multiple studies have demonstrated that targeted therapies might also modulate the immune response, such as attenuating the function of specific immune cell population, namely cytotoxic T lymphocytes and $Tr_M$s [23]. They influence T cell priming and also dictate their differentiation into memory and effector phenotypes, alongside augmenting antigen tumour presentation by dendritic cells enabling better sensitization of tumour cells to immune-mediated destruction [23]. While, the likely interplay of immunotherapy and targeted therapy remains to be fully elucidated, the synergism and toxicity profile of combination approaches will heavily depend on timing, sequence and dosage [23].

Of particular interest is mitogen-activated protein kinase (MAPK) pathway, which is known to upregulate production of IL-8 and VEGF which in turn induce inhibitory effects on T cell function and recruitment [24]. Recent studies have indicated that MEK1/2 inhibition selectively blocks naïve but not antigen-experienced effector T-cell activation [25]. In addition, independent studies have shown BRAF inhibitors to have immune-sensitization potential via the up-regulation of tumour antigen expression and presentation; an example can in case of melanoma where in MAPK upregulation results in upregulation of melanocyte differentiation antigens (MADs) [26, 27]. A recent study based on a murine model, demonstrated improved efficacy of pmel-1 ACT and BRAF inhibitor dabrafenib in combination with trametinib (MEK inhibitor), as the triple combination increased T cell infiltration into tumours, improved in vivo cytotoxicity and led to complete tumour regression in a syngeneic $BRAF^{V600E}$ driven melanoma mouse model [28]. In addition, Kang et al, have demonstrated that trametinib enhances MHC class I expression in human HNSCC cell lines in a STT3 dependent manner enabling better CD8+ T cell infiltration [29].

Independently, epigenetic modification of DNA using small molecule epigenetic modifiers can also alter the immune gene signature and impact antigen processing, presentation and immune evasion [30, 31]. Recently, Kagoya et al, have shown that the bromodomain and extra-terminal (BET) motif protein inhibitor, JQ1 maintains the functional properties of stem cell-like and central memory of CD8+ T cells [32]. Mechanistically, BRD4 (a BET protein) directly regulates BATF (a transcription factor) expression in CD8+ T cells as BATF dictates the differentiation process in T cells into effector memory phenotype. As such, JQ1 treated CD8+ T cells showed enhanced anti-tumour effects in murine adaptive T cell model against melanoma [32]. In addition, JQ1 is associated with downregulation of MYC in multiple cancers [33]. MYC, which has been shown to strongly regulate the tumour microenvironment by transcriptionally regulating immune modulators such as PD-L1 and CD47 [34]. Thus, MYC inhibition could strongly result in anti-tumour progression by downregulation of the hostile tumour microenvironment and promote immune-mediated tumour elimination.

Results

Combining MEK1/2 Inhibitor with EBV-Specific T Cells

Figure 7:
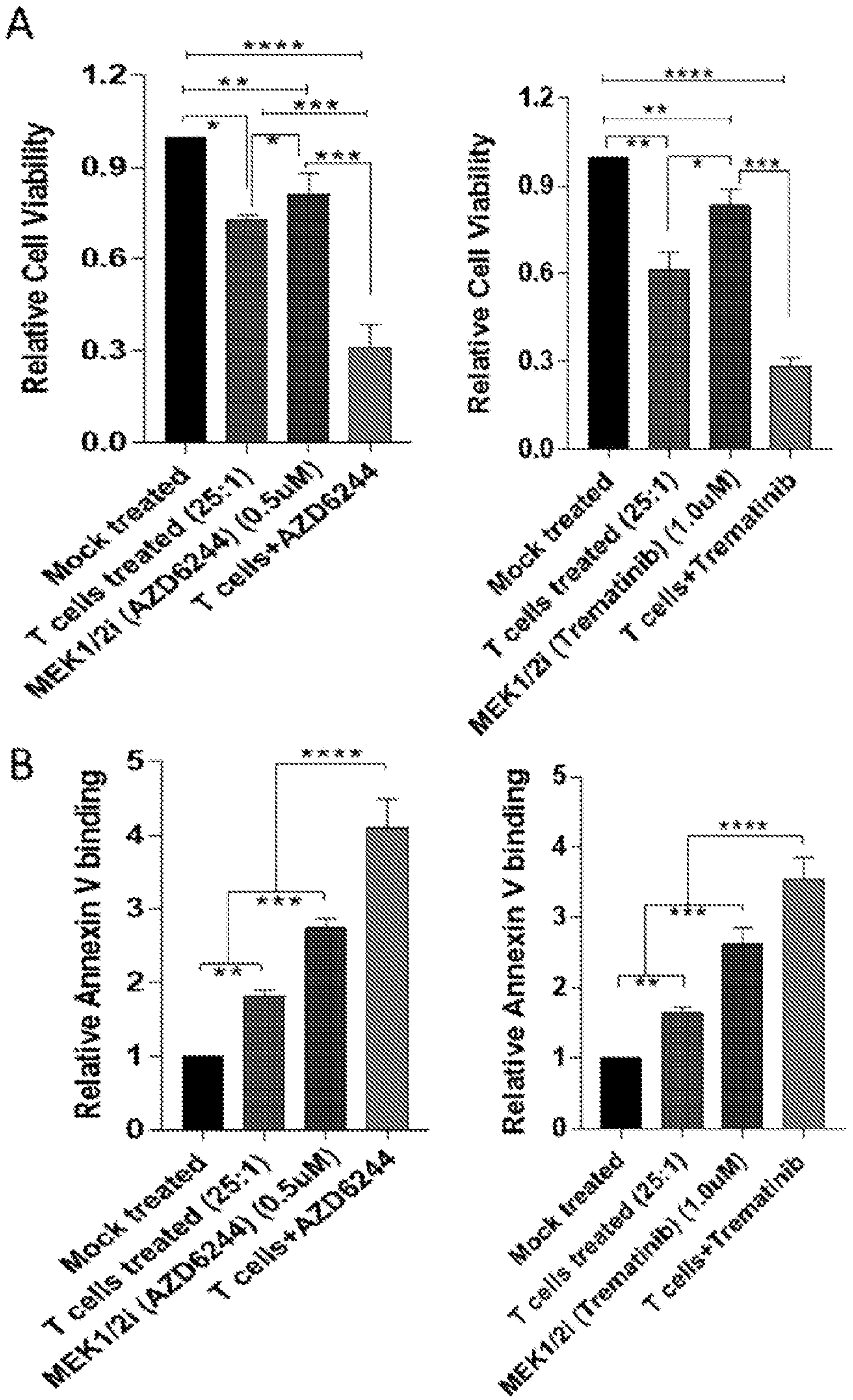
FIG. 7: Combination of MEK/12 inhibitors with EBV-specific T cells. (A) Statistical representation of the cell viability measured by MTS assay highlighting the impact of a HLA-matched EBV specific T cells and MEK1/2 inhibitors (AZD6244 and trametinib) in suppressing cellular growth individually and in combination after 48 hrs of incubation with SNU719 cells. (B) Statistical representation of cell death measured by Annexin V binding assay observed in presence EBV specific T cells and MEK1/2 inhibitors as individual and combination treatment highlighting the level of cell death observed after 48 hrs of incubation with SNU719 cells. (C) Growth curve highlight the rate of cellular death observed in the presence of HLA-matched EBV specific T cells and MEK1/2 inhibitors individually and in combination using Xcellegence. P-values were calculated using one-way ANOVA: *p<0.05, p<0.01, *p<0.001 and ****p<0.0001.
Figure 7:
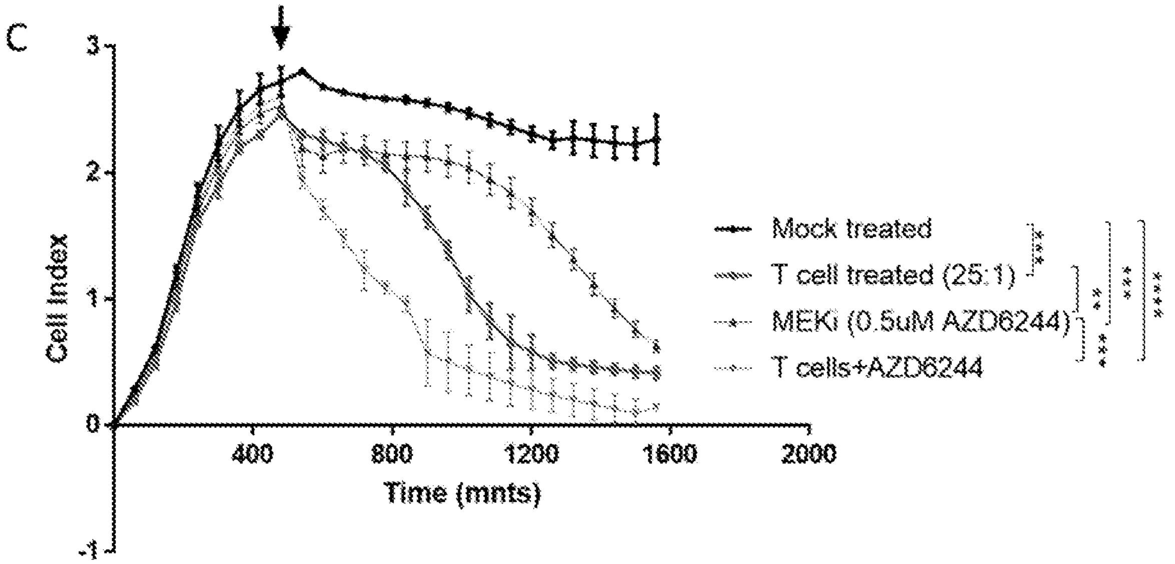

We treated SNU719 cells (gastric cancer cells) with MEK1/2 inhibitor (AZD6244 (or selumetanib) and trematinib) at concentration of 0.5 μM and 1.0 μM respectively, as individual treatment or in combination with EBV-specific T cells (25:1) as effector to target ratio. We observed that the cell viability of SNU719 was significantly reduced in presence of the combination of MEK1/2 inhibitor and EBV-specific T cells compared the individual treatment (FIG. 7A). Similarly, we observed that the dual combination group resulted in significantly higher binding of Annexin V among the SNU719 cells compared to individually treatment groups (FIG. 7B). In addition, using Xcellegence, we observed that the dual combination resulted in faster cell death among SNU719 cells compared to individual treatment of either MEK1/2 inhibitor or EBV-specific T cells (FIG. 7C). Collectively, these results highlight the efficacy of the dual combination of MEK1/2 inhibition with EBV-specific T cells in vitro.

Combining JQ1 Inhibitor with EBV-Specific T Cells

Figure 8:
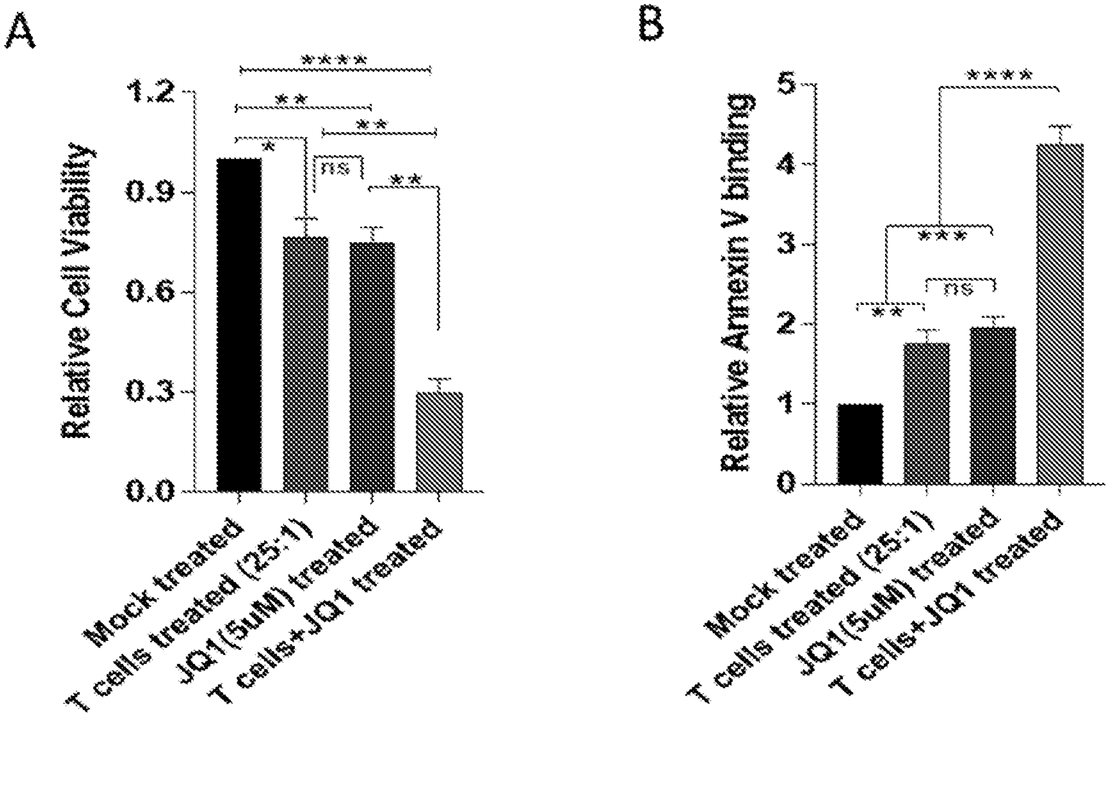
FIG. 8: Combination of JQ1 with EBV-specific T cells. (A) Statistical representation of the cell viability measured by MTS assay highlighting the impact of a HLA-matched EBV specific T cells and JQ1 in suppressing cellular growth individually and in combination after 48 hrs of incubation with SNU719 cells. (B) Statistical representation of cell death measured by Annexin V binding assay observed in presence EBV specific T cells and JQ1 as individual and combination treatment highlighting the level of cell death observed after 48 hrs of incubation with SNU719 cells. P-values were calculated using one-way ANOVA: ns—not significant, *p<0.05, p<0.01, *p<0.001 and ****p<0.0001.

We treated SNU719 cells with JQ1 inhibitor at concentration of 5.0 μM, as individual treatment or in combination with EBV-specific T cells (25:1) as effector to target ratio. We observed that the cell viability of SNU719 was significantly reduced in presence of the combination of JQ1 inhibitor and EBV-specific T cells compared the individual treatment (FIG. 8A). Similarly, we observed that the dual combination group resulted in significantly higher binding of Annexin V among the SNU719 cells compared to individually treatment groups (FIG. 8B). Collectively, these results highlight the efficacy of the dual combination of BET inhibition with EBV-specific T cells in vitro.

Example 3

Figure 9:
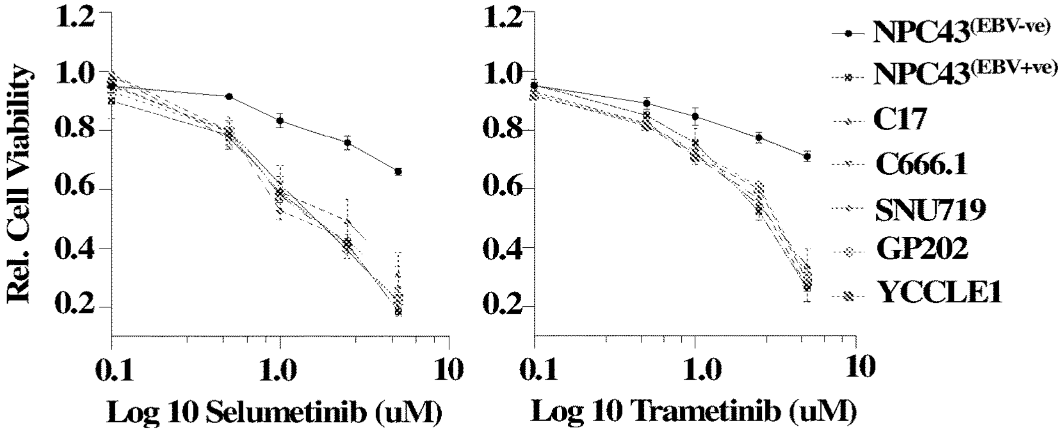
FIG. 9: Determining the ICso value of MEK1/2 inhibitors. Representation of the cell viability performed using MTS assay after the indicated cell lines were incubated with 0.1 μM-5 μM of selumatinib (left panel) and trametinib (right panel) for 48 hours. The data are represented as the mean±SD from three independent experiments.
Figure 10:
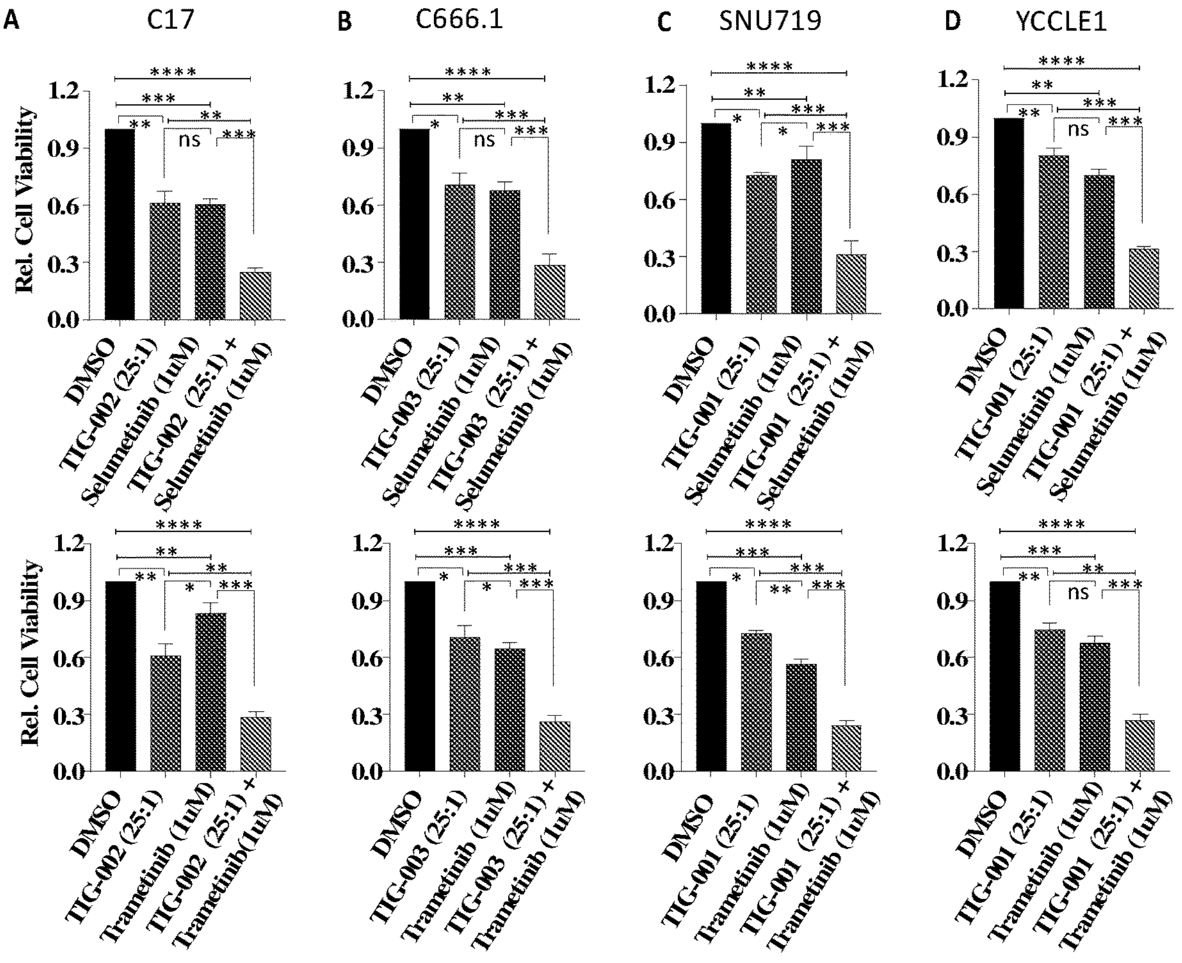
FIG. 10: Combination of MEK1/2 inhibitors with HLA matched allogeneic EBV-specific T cells. The cell viability measured by MTS assay highlighting the impact of a HLA-matched EBV specific T cells at the effector-to-target ratio of 25:1 and MEK1/2 inhibitors selumatinib (upper panel) and trametinib (lower panel) at a concentration of 1 μM in suppressing cellular growth individually and in combination after 48 hrs of incubation with indicated (A) C17; (B) C666.1; (C) SNU719 and (D) YCCLE1. The data are represented as the mean±SD from three independent experiments. P-values were calculated using one-way ANOVA: ns=not significant, *=p<0.05, =p<0.01, *=p<0.001 and ****=p<0.0001.

To determine the upregulation of MAPK pathway in EBV-associated solid cancers, we first identified the $IC_{50}$ value of MEK1/2 inhibitors (AZD6244 or selumetanib and trematinib) across nasopharyngeal and gastric cancer cell lines (with drug concertation ranging from 0.1 μM-5 μM). We observed that compared to $NPC43^{(EBV-)}$ cell line, EBV-associated cell lines uniformly demonstrated high dependency on MAPK pathway as both the inhibitors achieved ~50% reduction in cell viability ($IC_{50}$) at a concertation of ~2.5 μM using MTS assay (FIG. 9). In the next set of experiments, we wanted to determine the impact of MEK1/2 inhibition in combination with allogeneic EBV-specific T cells on EBV-associated solid cancers. As such, we treated the respective EBV-associated cell lines (both gastric and nasopharyngeal) individually or in combination with MEK1/2 inhibitors (both selumetanib and trematinib) and EBV-specific T cells. We chose the sub $IC_{50}$ value (or $IC_{25}$ value) of the respective MEK1/2 inhibitors (1 μM) alongside an effector to target ratio of 25:1 of the respective HLA matched allogeneic EBV-specific T cells for the in vitro treatment. We observed that the cell viability of the respective nasopharyngeal (C17 and C666.1) and gastric cancer cells (SNU719 and YCCLE1) was significantly reduced in presence of the combination of MEK1/2 inhibitors and EBV-specific T cells compared the individual treatment (FIG. 10).

Figure 11:
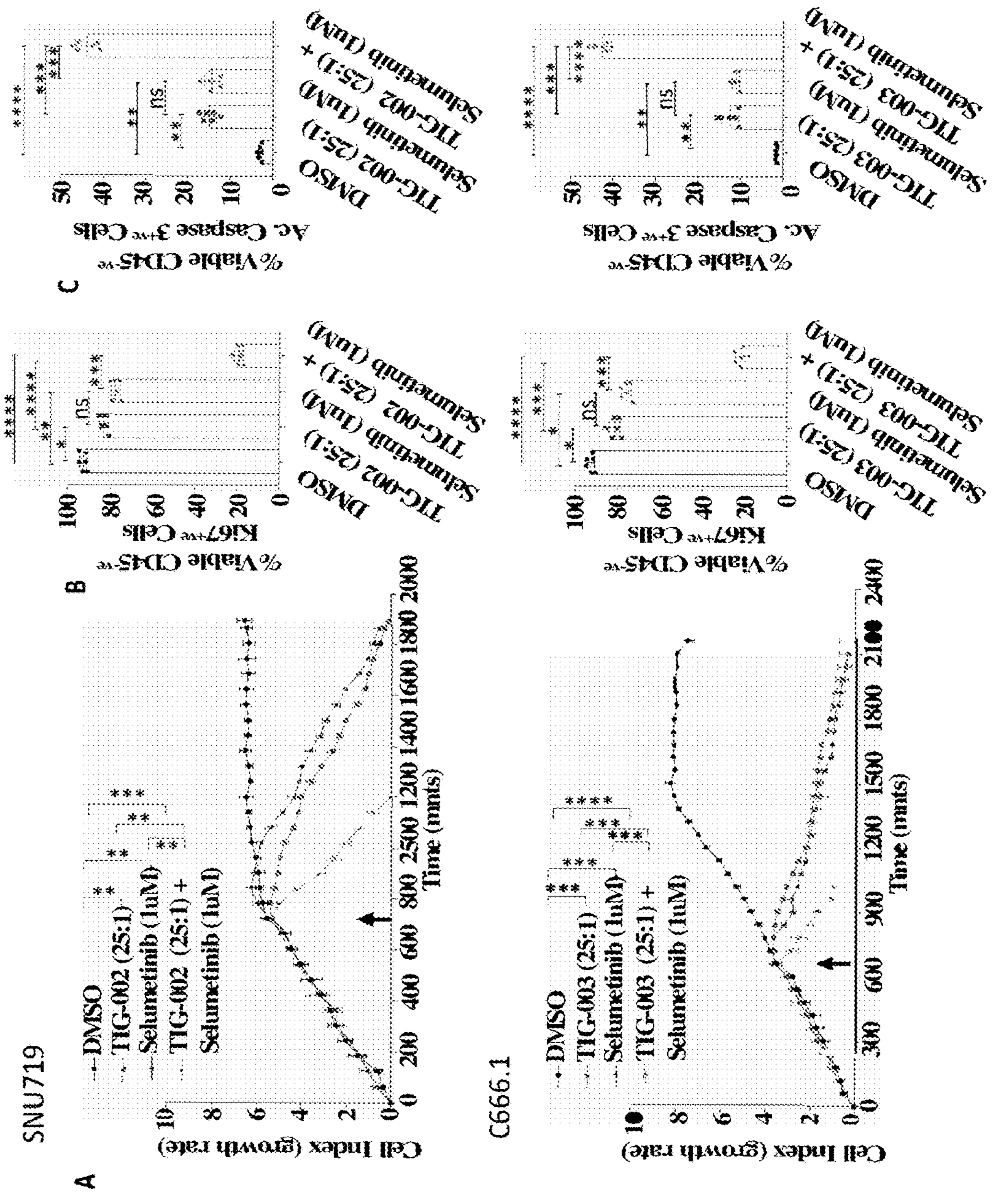
FIG. 11: Impact of dual combination of MEK1/2 inhibitor and HLA matched allogeneic EBV-specific T cells. (A) Cell growth curve highlight the rate of cellular proliferation of SNU719 (upper panel) and C666.1 (lower panel) observed in the presence of HLA-matched EBV specific T cells (effector-to-target ratio of 25:1) and selumatinib (1 μM) individually and in combination, measured using Xcellegence. The effect of individual and dual combination on (B) cell proliferation based on Ki67 and (C) cell death based on active Caspase-3 of SNU719 expression (upper panel) and C666.1 (lower panel), performed using flow cytometry. The data are represented as the mean±SD from three independent experiments. P-values were calculated using one-way ANOVA: ns=not significant, *p<0.05, p<0.01, *p<0.001 and ****p<0.0001.

Further, to validate the impact of the combination on the cell proliferation of the EBV-associated cancer cells, we challenged SNU719 and C666.1 cells with individual and dual combination using Xcellegence. We observed that the dual combination resulted in faster cell death of SNU719 and C666.1 cells compared to individual treatment of either MEK1/2 inhibitor (selumatinib) or HLA matched EBV-specific T cells (FIG. 11A). We also performed phenotypic characterization, using flow cytometry, of SNU719 and C666.1 cells after 16 hours of individual and dual treatment in vitro. We observed that the dual treatment resulted in significant loss of cell proliferation (indicated by $Ki67^{+}$ staining) and caused significant cell death as indicated Active Caspase 3 staining, compared to individual treatment (FIG. 11B-C).

Figure 12:
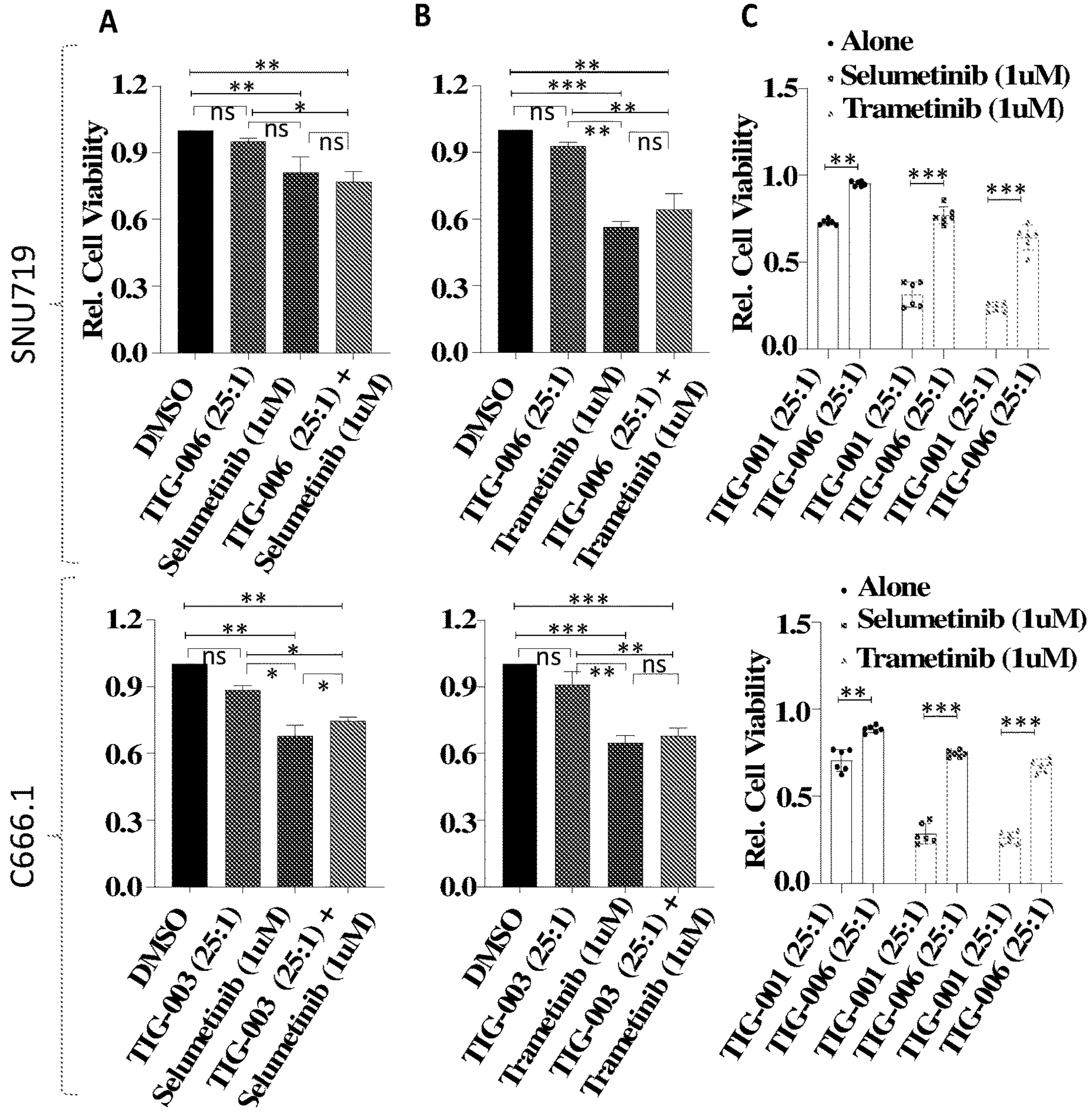
FIG. 12: Combination of MEK1/2 inhibitors with HLA mismatched allogeneic-specific T cells. The cell viability measured by MTS assay highlighting the impact of a HLA-mismatched specific T cells at the effector-to-target ratio of 25:1 and MEK1/2 inhibitors (A) selumatinib and (B) trametinib at a concentration of 1 μM in suppressing cellular growth individually and in combination after 48 hrs of incubation with SNU719 (upper panel) and C666.1 (lower panel). (C) The cell viability measured by MTS assay comparing the effect of HLA-matched and HLA-mismatched EBV-specific T cells (at the effector-to-target ratio of 25:1) alone and in combination with selumatinib and trametinib (1 μM) when incubated with SNU719 (upper panel) and C666.1 (lower panel). The data are represented as the mean±SD from three independent experiments. P-values were calculated using one-way ANOVA: ns=not significant, *=p<0.05, =p<0.01, *=p<0.001 and ****=p<0.0001.

Next, we wanted to determine the specificity of the combination and as such we challenged SNU719 and C666.1 cells with HLA-mismatched allogeneic T cells alongside MEK1/2 inhibitors (both selumetanib and trematinib), individually and in combination. We observed that the HLA-mismatched allogeneic T cells individually did not have significant impact on the cell viability of the EBV-associated cancer cells (FIG. 12A-B). Interestingly, we observed significant reduction in cell viability of the cancer cells in presence of the dual combination of MEK1/2 inhibitors and HLA-mismatch allogeneic T cells compared to DMSO treated (control) cancer cells (FIG. 12A-B). However, the reduced cell viability observed in the presence of dual combination demonstrated no significant reduction in cell viability compared to treatment of MEK1/2 inhibitors alone (FIG. 12A-B). This data highlights that the reduced cell viability observed in the presence of dual combination in induced due to inhibition of MAPK pathway alone and the addition of HLA-mismatched T cells did not enhance the efficacy of the combination. To further validate this concept, we compared the reduction in cell viability of the EBV-associated cancer cells (SNU719 and C666.1) caused by the respective HLA-matched and HLA-mismatched T cells alone and in combination with MEK1/2 inhibitors (both selumetanib and trematinib). We observed that alone, the HLA-matched T cells induced significant cell death compared HLA-mismatched T cells and this effect is significantly amplified in presence of either selumetanib or trematinib (FIG. 12C).

Figure 13:
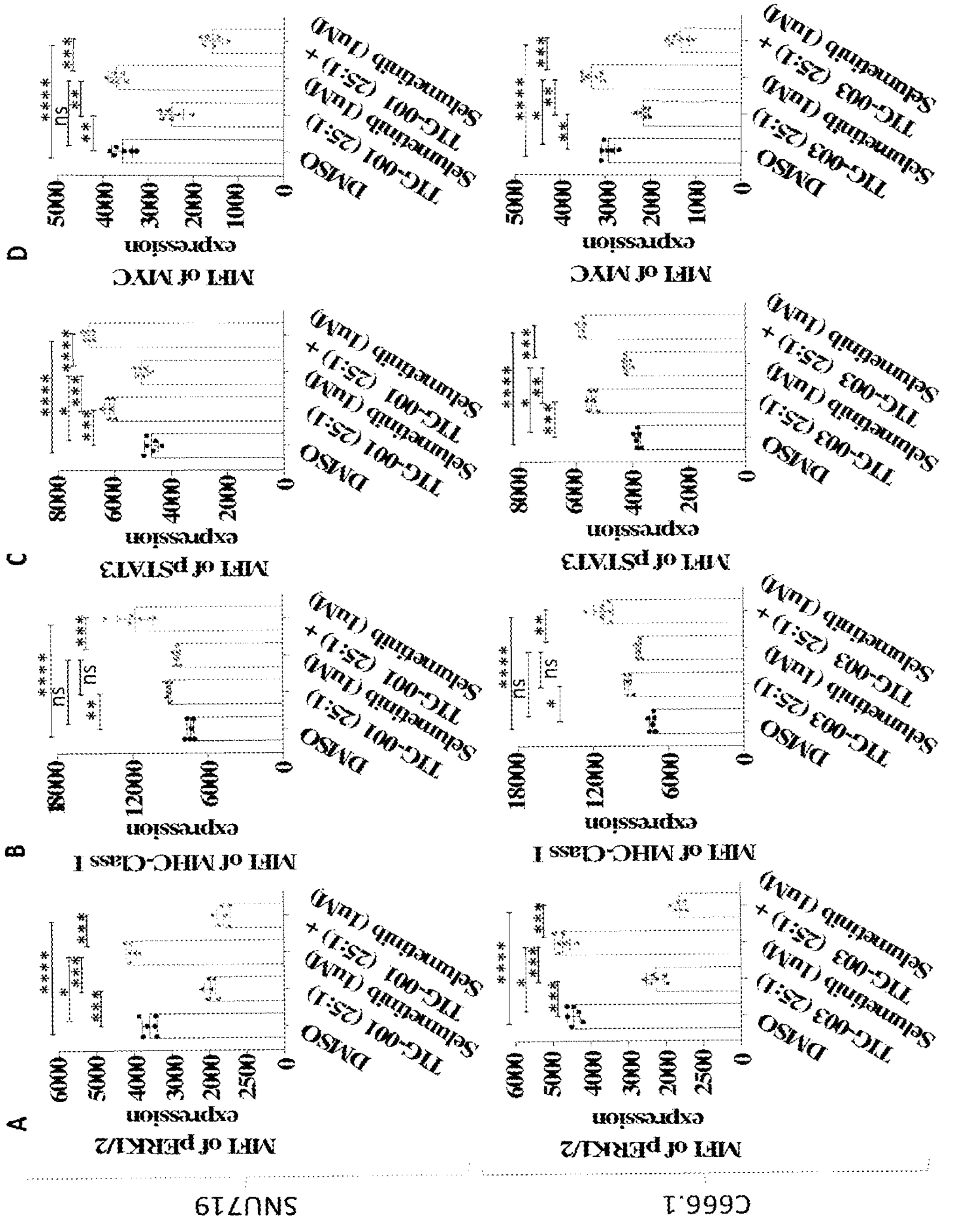
FIG. 13: Phenotyping the impact of dual combination of MEK1/2 inhibitor and HLA matched allogeneic EBV-specific T cells on cancer cell intrinsic pathways. Representation of the cancer cell phenotype after 16 hours of individual and dual combination of selumatinib (1 μM) and HLA-matched EBV specific T cells (effector-to-target ratio of 25:1) among SNU719 (upper panel) and C666.1 (lower panel) on the expression of (A) pERK1/2; (B) MHC-Class I; (C) pSTAT3; and (D) MYC performed using flow cytometry. The data are represented as the mean±SD from three independent experiments. P-values were calculated using one-way ANOVA: ns=not significant, *p<0.05, p<0.01, *p<0.001 and ****p<0.0001.

In next set of experiments, we wanted to investigate the effect of the dual combination the cancer cell intrinsic pathway and describe the rationale of the effective combination of MEK1/2 inhibition with T cell treatment. We observed that the presence of MEK1/2 inhibitor (selumatinib) resulted in significant reduction of pERK1/2 (FIG. 13A) in the cancer cells, after 16 hours of treatment. As a result, we observed upregulation of MHC-Class I expression in presence of selumatinib alone and in combination with respective HLA-matched T cells (FIG. 13B). To validate the mechanism via which MHC-Class I expression is upregulated in these cancer cells, we investigated the impact of MEK1/2 inhibition on pSTAT3 and MYC expression. We observed that presence salumatinib resulted in upregulation of pSTAT3 expression (FIG. 13C), which has been shown to be associated with driving MHC-class I expression [29, 35, 36]. In addition, we also observed that MEK1/2 inhibition resulted in downregulation of MYC expression (FIG. 13D). Presence of MYC expression has been shown to downregulate MHC-class I expression in EBV-associated cancers and therefore its indirect inhibition probably assist MHC-class I in these cancers [37]. Thus, inhibition of MEK1/2 pathway results in upregulation of MHC-class I expression via upregulation of STAT3 pathway and downregulation of MYC which enabling better therapeutic compatibility in presence of HLA-matched allogeneic T cells. Collectively, these results highlight the efficacy of the dual combination of MEK1/2 inhibition with EBV-specific T cells in vitro.

Figure 14:
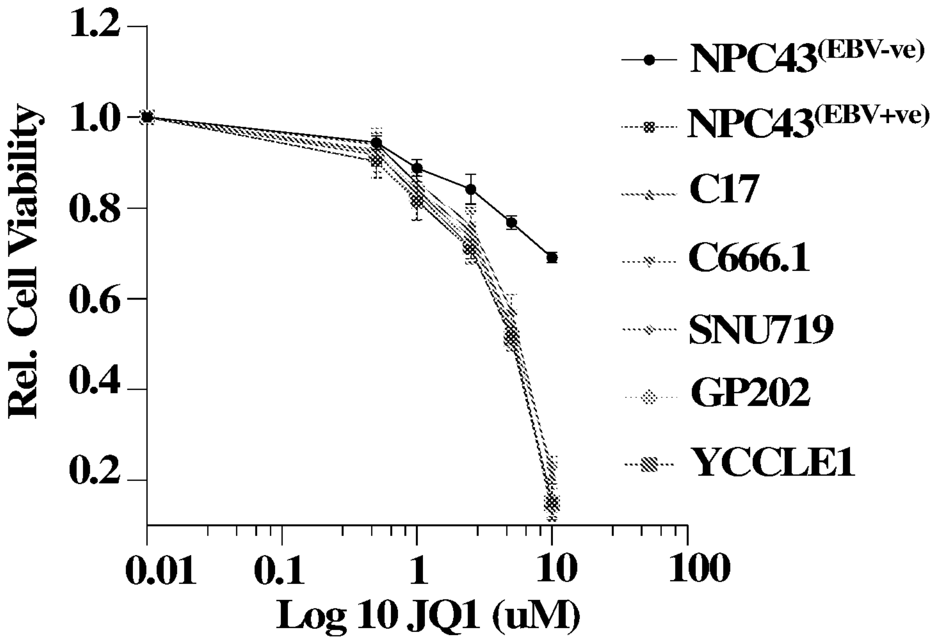
FIG. 14: Determining the $IC_{50}$ value of JQ1 inhibitors. Representation of the cell viability performed using MTS assay after the indicated cell lines were incubated with 0.5 μM-10 μM of JQ1 for 48 hours. The data are represented as the mean±SD from three independent experiments.
Figure 15:
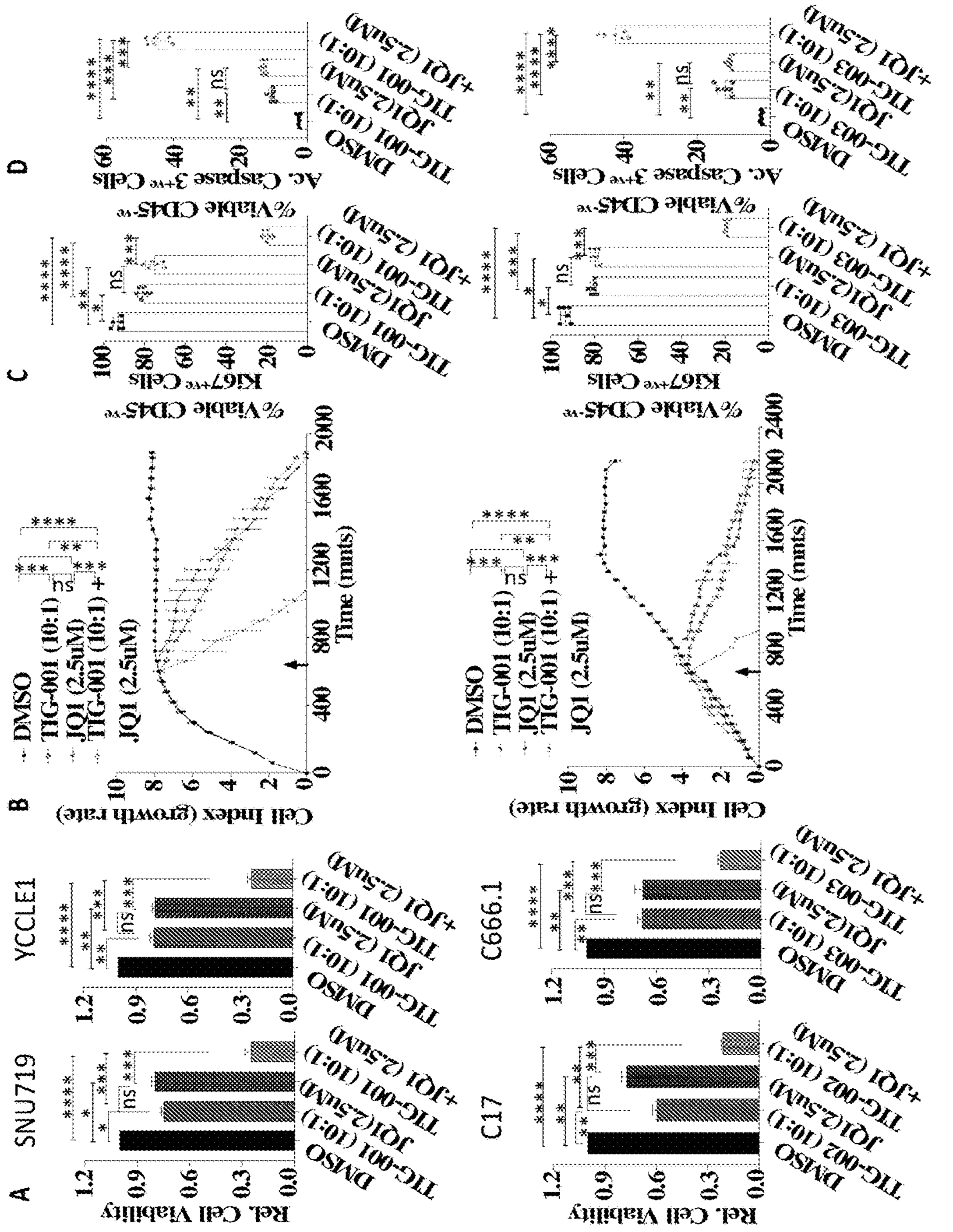
FIG. 15: Impact of dual combination of JQ1 inhibitor and HLA matched allogeneic EBV-specific T cells. The cell viability measured by MTS assay highlighting the impact of a HLA-matched EBV specific T cells at the effector-to-target ratio of 25:1 and JQ1 (2.5 μM) in suppressing cellular growth individually and in combination after 48 hrs of incubation with indicated (A) gastric (SNU719, YCCLE1 (upper panel)) and nasopharyngeal cancer cells (C17, C666.1 (lower panel)). (B) Cell growth curve highlight the rate of cellular proliferation of SNU719 (upper panel) and C666.1 (lower panel) observed in the presence of HLA-matched EBV specific T cells (effector-to-target ratio of 25:1) and JQ1 (2.5 μM) individually and in combination, measured using Xcellegence. The effect of individual and dual combination on (C) cell proliferation based on Ki67 and (D) cell death based on active Caspase-3 of SNU719 expression (upper panel) and C666.1 (lower panel), performed using flow cytometry. The data are represented as the mean±SD from three independent experiments. P-values were calculated using one-way ANOVA: ns=not significant, *p<0.05, p<0.01, *p<0.001 and ****p<0.0001.

Similarly, we targeted MYC-dependent cancer intrinsic pathway using JQ1 inhibitor by first determining the $IC_{50}$ value of the inhibitor across nasopharyngeal and gastric cancer cell lines (with drug concertation ranging from 0.5 μM-10 μM). We observed that the JQ1 inhibitor demonstrated ~50% reduction in cell viability ($IC_{50}$) at a concertation of ~2.5 μM among the EBV-associated cell lines compared to $NPC43^{(EBV-)}$ cell line (FIG. 14). To characterized the impact of JQ1 inhibition in combination with allogeneic EBV-specific T cells on EBV-associated cancer cells, we used $IC_{25}$ value JQ1 (2.5 μM) alongside an effector to target ratio of 25:1 of the respective HLA matched allogeneic EBV-specific T cells in vitro. We observed that the cell viability of the respective gastric cancer cells (SNU719 and YCCLE1) and nasopharyngeal (C17 and C666.1) was significantly reduced in presence of the combination of JQ1 inhibitor and EBV-specific T cells compared the individual treatment (FIG. 15A). Further, using Xcellegence, we observed that the dual combination resulted in faster cell death of SNU719 and C666.1 cells compared to individual treatment (FIG. 15B). We also performed phenotypic characterization, using flow cytometry, of SNU719 and C666.1 cells after 16 hours of individual and dual treatment in vitro. We observed that the dual treatment resulted in significant loss of cell proliferation (indicated by $Ki67^{+}$ staining) and caused significant cell death as indicated Active Caspase 3 staining, compared to individual treatment (FIG. 15B-C).

Figure 16:
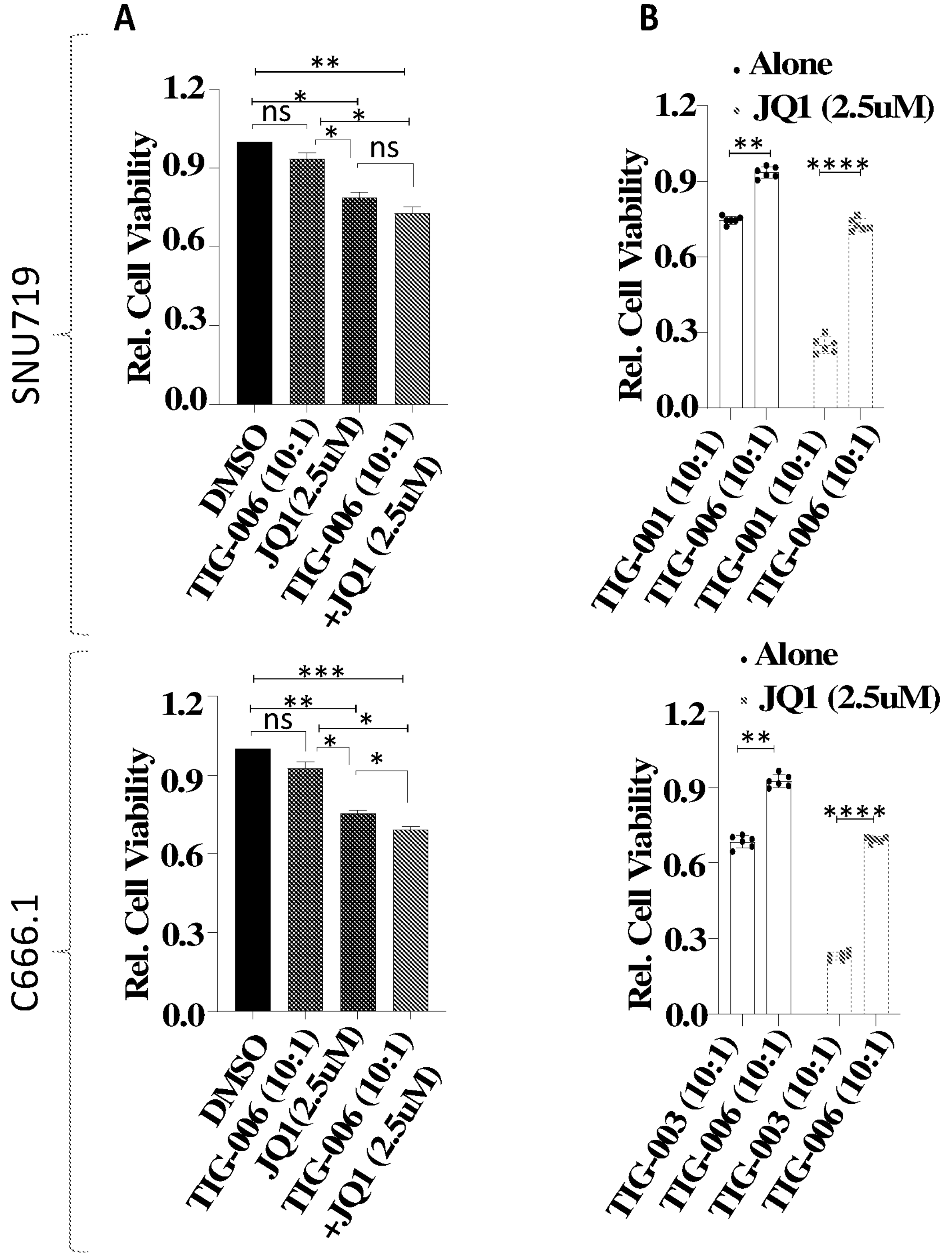
FIG. 16: Combination of JQ1 inhibitors with HLA mismatched allogeneic-specific T cells. (A) The cell viability measured by MTS assay highlighting the impact of a HLA-mismatched specific T cells at the effector-to-target ratio of 25:1 and JQ1 inhibitor at a concentration of 2.5 μM in suppressing cellular growth individually and in combination after 48 hrs of incubation with SNU719 (upper panel) and C666.1 (lower panel). (B) The cell viability measured by MTS assay comparing the effect of HLA-matched and HLA-mismatched EBV-specific T cells (at the effector-to-target ratio of 25:1) alone and in combination with JQ1 inhibitor (2.5 μM) when incubated with SNU719 (upper panel) and C666.1 (lower panel). The data are represented as the mean f SD from three independent experiments. P-values were calculated using one-way ANOVA: ns=not significant, *=p<0.05, =p<0.01, *=p<0.001 and ****=p<0.0001.
Figure 17:
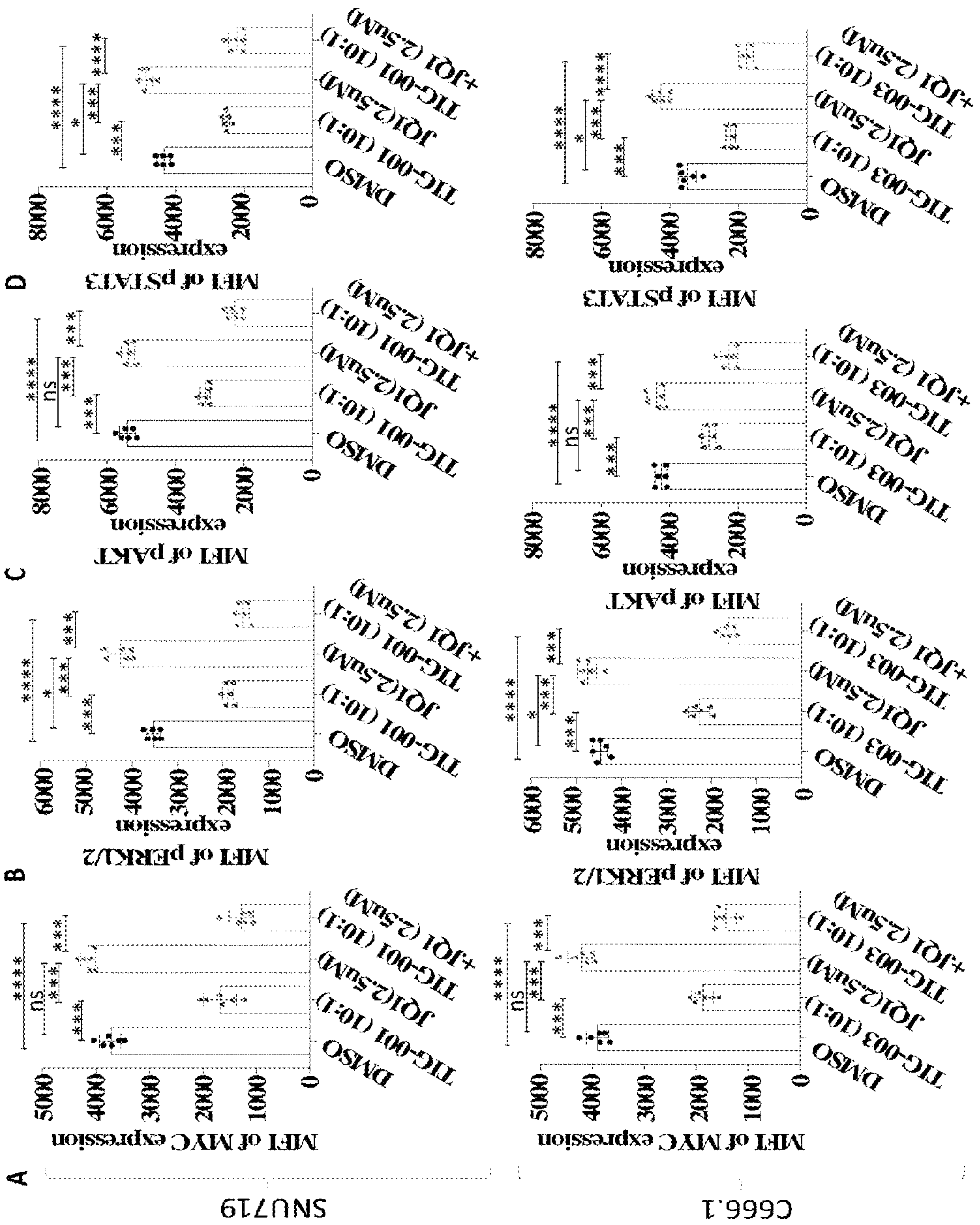
FIG. 17: Phenotyping the impact of dual combination of JQ1 inhibitor and HLA matched allogeneic EBV-specific T cells on cancer cell intrinsic pathways. Representation of the cancer cell phenotype after 16 hours of individual and dual combination of JQ1 (2.5 μM) and HLA-matched EBV specific T cells (effector-to-target ratio of 25:1) among SNU719 (upper panel) and C666.1 (lower panel) on the expression of (A) MYC; (B) pERK1/2; (C) pAKT; and (D) pSTAT3 performed using flow cytometry. The data are represented as the mean±SD from three independent experiments. P-values were calculated using one-way ANOVA: ns=not significant, *p<0.05, p<0.01, *p<0.001 and ****p<0.0001.
Figure 18:
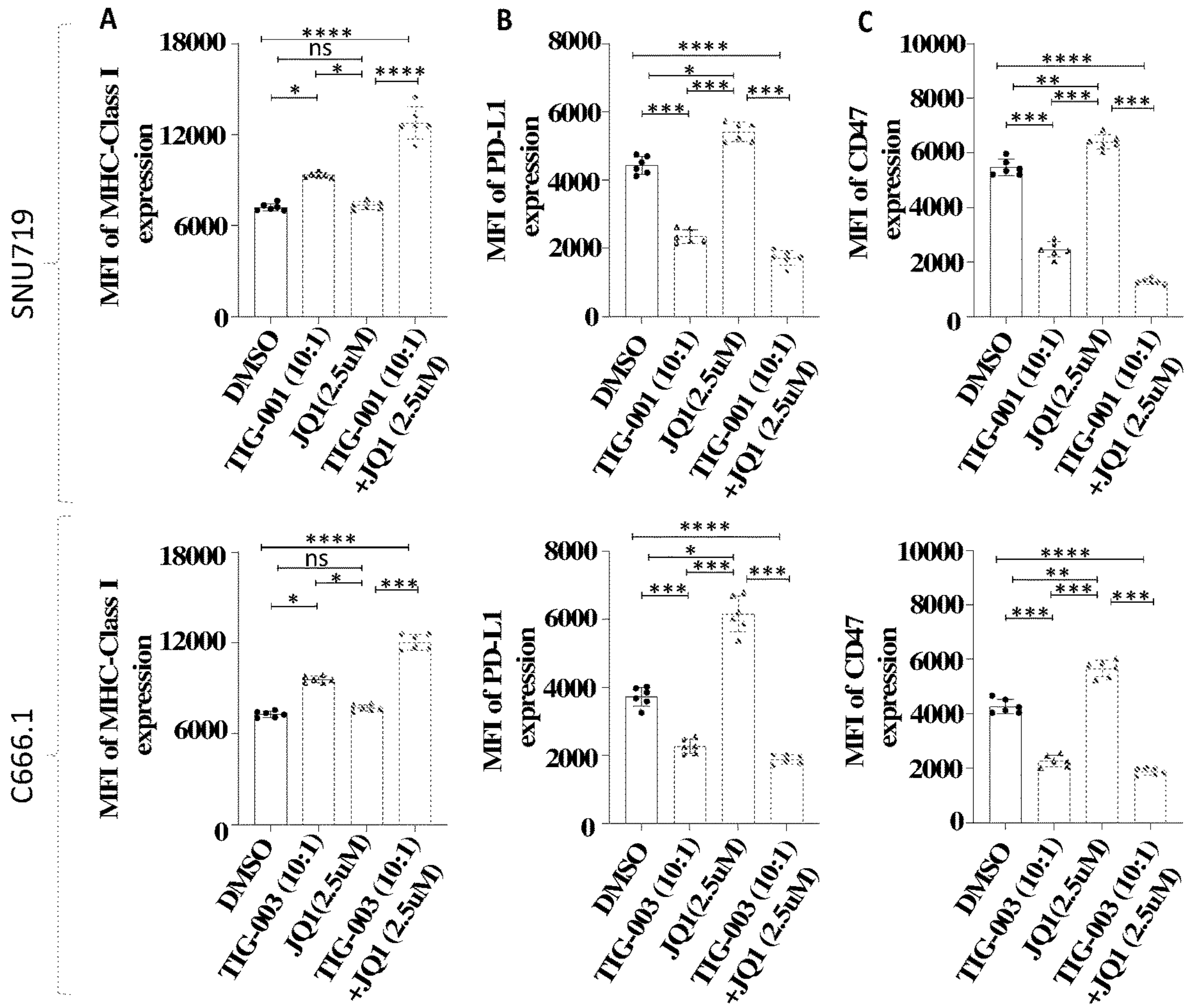
FIG. 18: Phenotyping the impact of dual combination of JQ1 inhibitor and HLA matched allogeneic EBV-specific T cells on immune regulatory molecules. Representation of the cancer cell phenotype after 16 hours of individual and dual combination of JQ1 (2.5 μM) and HLA-matched EBV specific T cells (effector-to-target ratio of 25:1) among SNU719 (upper panel) and C666.1 (lower panel) on the expression of (A) MHC Class-I; (B) PD-L1; and (C) CD47 performed using flow cytometry. The data are represented as the mean±SD from three independent experiments. P-values were calculated using one-way ANOVA: ns=not significant, *p<0.05, p<0.01, *p<0.001 and ****p<0.0001.

Next, we wanted to determine the specificity of the combination and as such we challenged SNU719 and C666.1 cells with HLA-mismatch allogeneic T cells alongside JQ1 inhibitor individually and in combination. Consistent to our previous data with MEK1/2 inhibitors, we observed significant reduction in cell viability of the cancer cells in presence of the combination of JQ1 inhibitor and HLA-mismatch allogeneic T cells compared to DMSO treated (control) cancer cells (FIG. 16A). However, the reduced cell viability observed in the presence of dual combination demonstrated no significant reduction in cell viability compared to treatment of JQ1 inhibitor alone (FIG. 16A). We observed that alone, the HLA-matched T cells induced significant cell death compared HLA-mismatched T cells and this effects is significantly amplified in presence of JQ1 (FIG. 16B). In next set of experiments, we wanted to investigate rationale of the effective combination of JQ1 inhibition with T cell treatment. We observed that the presence of JQ1 inhibitor resulted in significant reduction of MYC expression (FIG. 17A) in the cancer cells, after 16 hour of treatment. As a result, it caused downregulation of pERK1/2, pAKT and pSTAT3 expression (FIG. 17B-C). In addition, we also observed that downregulation of MYC resulted in enhancing MHC-class I (FIG. 18A) in these cancers, as discussed above [37]. Notably, we also observed downregulation of immune-regulatory molecules such as PD-L1 and CD47 expression (FIG. 18B-C). Therefore, loss of MYC expression enhances the efficacy of cytotoxic T cells by enhancing MHC-Class I expression downregulating immune-evasion molecules making the combination to be highly effective. Collectively, these results highlight the efficacy of the dual combination of JQ1 inhibition with EBV-specific T cells in vitro.

Figure 19:
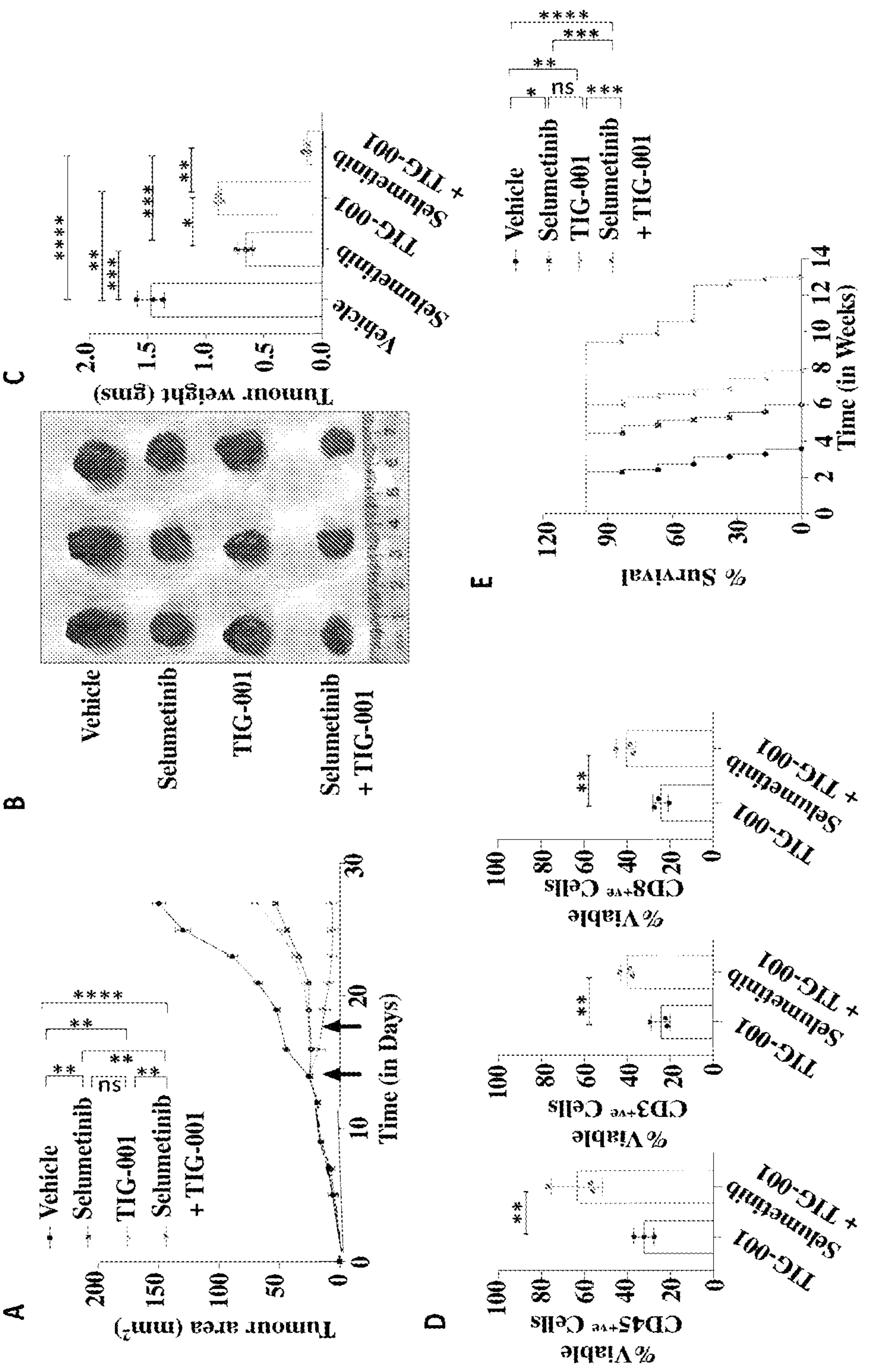
FIG. 19: Assessment of therapeutic efficacy of dual combination of selumatinib and allogeneic EBV-specific cytotoxic T cells in vivo. (A) The impact of the dual combination of selumatinib and allogeneic T cells (TIG-001) on the outgrowth of EBV-positive SNU719 xenografts in NRG mice was assessed. Tumour-bearing mice were treated with two doses of HLA-matched T cells ($2\times10^7$ T cells per dose per mouse indicated by black arrow) and selumatinib (12.5 mg/Kg) orally for continuous 14 days, either individually or in combination. The growth of each xenograft is represented as the mean tumour area ±SD from n=9 mice/group. (B) Gross morphology of the tumours isolated from the mice of indicated treatment groups. (C) Representation of tumour weight described in (B) from the mice of indicated treatment groups. The data are represented as the mean±SD from n=3 mice per group. P-values were calculated using one-way ANOVA. (D) Representation of viable percentage of tumour infiltrates observed across individually treated allogeneic T cells (TIG-001) and in combination with selumatinib as determined by CD45, CD3 and CD8 expression using flow cytometry. P-values were calculated using Student T test. (E) Kaplan-Meier overall survival analysis of the mice bearing EBV-associated tumours as described in (A) following individual and combination treatment of selumatinib and allogeneic T cells. The animals' survival (n=6 mice/group) was monitored over the indicated period of time and statistical significance was analysed by log-rank test: ns=not significant, *p<0.05, p<0.01, *p<0.001 and ****p<0.0001.

In next set of experiments, we wanted to investigate the effect of the above described small molecules in combination of HLA matched allogeneic EBV-specific T cells in vivo. We used the combination of selumatinib and HLA-matched T cell product (TIG-001) to treat SNU719 derived xenograft tumour model in female NRG mice. Once the xenograft reached the size of ~25 $mm^2$, we treated the mice with two infusion of TIG-001 ($2\times10^7$ cells per infusion) individually and in combination with daily dosage selumatinib (12.5 mg/kg), administered orally for 14 days. We observed that the dual combination resulted in significant reduction in tumour progression of compared to individual treatment (FIG. 19A). We sacrificed three mice from each group when the control reached the ethical size limit of 150 $mm^2$ and comparatively we observed the size of the tumours in the dual combination group to be significantly smaller compared to individual treatment (FIG. 19B-C). Next, we phenotyped the infiltration of the human origin lymphocytes in these tumours using flow cytometry. We observed that the combination group demonstrated significantly more number of viable CD45+CD3+CD8+ cells compared to individually treated T cell group (FIG. 19D). We also performed long term monitoring of these post therapy (the mice from each group were monitored for tumour progression up to the ethical size limit of 150 $mm^2$) and observed that the dual combination group demonstrated better survival rate compared to individual treatment group (FIG. 19E).

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

REFERENCES

[1] C. S. Azimi, Q. Tang, K. T. Roybal, J. A. Bluestone, NextGen cell-based immunotherapies in cancer and other immune disorders, Curr Opin Immunol, 59 (2019) 79-87.
[2] M. E. Dudley, J. R. Wunderlich, T. E. Shelton, J. Even, S. A. Rosenberg, Generation of tumor-infiltrating lymphocyte cultures for use in adoptive transfer therapy for melanoma patients, J Immunother, 26 (2003) 332-342.
[3] S. K. Parida, T. Poiret, L. Zhenjiang, Q. Meng, J. Heyckendorf, C. Lange, A. S. Ambati, M. V. Rao, D. Valentini, G. Ferrara, E. Rangelova, E. Dodoo, A. Zumla, M. Maeurer, T-Cell Therapy: Options for Infectious Diseases, Clin Infect Dis, 61Suppl 3 (2015) S217-224.
[4] M. Hale, T. Mesojednik, G. S. Romano Ibarra, J. Sahni, A. Bernard, K. Sommer, A. M. Scharenberg, D. J. Rawlings, T. A. Wagner, Engineering HIV-Resistant, Anti-HIV Chimeric Antigen Receptor T Cells, Mol Ther, 25 (2017) 570-579.
[5] C. Smith, G. Okern, S. Rehan, L. Beagley, S. K. Lee, T. Aarvak, K. W. Schjetne, R. Khanna, Ex vivo expansion of human T cells for adoptive immunotherapy using the novel Xeno-free CTS Immune Cell Serum Replacement, Clin Transl Immunology, 4 (2015) e31.
[6] O. M. Pello, A. J. Innes, A. Bradshaw, S. A. Finn, S. Uddin, E. Bray, E. Olavarria, J. F. Apperley, J. Pavlu, BKV-specific T cells in the treatment of severe refractory haemorrhagic cystitis after HLA-haploidentical haematopoietic cell transplantation, Eur J Haematol, 98 (2017) 632-634.
[7] C. Smith, R. Khanna, Adoptive cellular immunotherapy for virus-associated cancers: a new paradigm in personalized medicine, Immunol Cell Biol, 95 (2017) 364-371.
[8] R. Khanna, S. R. Burrows, M. G. Kurilla, C. A. Jacob, I. S. Misko, T. B. Sculley, E. Kieff, D. J. Moss, Localization of Epstein-Barr virus cytotoxic T cell epitopes using recombinant vaccinia: implications for vaccine development, J Exp Med, 176 (1992) 169-176.
[9] R. J. Murray, M. G. Kurilla, J. M. Brooks, W. A. Thomas, M. Rowe, E. Kieff, A. B. Rickinson, Identification of target antigens for the human cytotoxic T cell response to Epstein-Barr virus (EBV): implications for the immune control of EBV-positive malignancies, J Exp Med, 176 (1992) 157-168.
[10] M. P. Thompson, R. Kurzrock, Epstein-Barr virus and cancer, Clin Cancer Res, 10 (2004) 803-821.
[11] C. Smith, J. Tsang, L. Beagley, D. Chua, V. Lee, V. Li, D. J. Moss, W. Coman, K. H. Chan, J. Nicholls, D. Kwong, R. Khanna, Effective treatment of metastatic forms of Epstein-Barr virus-associated nasopharyngeal carcinoma with a novel adenovirus-based adoptive immunotherapy, Cancer Res, 72 (2012) 1116-1125.
[12] C. Smith, L. Cooper, M. Burgess, M. Rist, N. Webb, E. Lambley, J. Tellam, P. Marlton, J. F. Seymour, M. Gandhi, R. Khanna, Functional reversion of antigen-specific CD8+ T cells from patients with Hodgkin lymphoma following in vitro stimulation with recombinant polyepitope, J Immunol, 177 (2006) 4897-4906.
[13] M. Kalimutho, D. Sinha, J. Jeffery, K. Nones, S. Srihari, W. C. Fernando, P. H. Duijf, C. Vennin, P. Raninga, D. Nanayakkara, D. Mittal, J. M. Saunus, S. R. Lakhani, J. A. Lopez, K. J. Spring, P. Timpson, B. Gabrielli, N. Waddell, K. K. Khanna, CEP55 is a determinant of cell fate during perturbed mitosis in breast cancer, EMBO Mol Med, (2018).
[14] S. M. Smith, M. B. Wunder, D. A. Norris, Y. G. Shellman, A simple protocol for using a LDH-based cytotoxicity assay to assess the effects of death and growth inhibition at the same time, PLoS One, 6 (2011) e26908.
[15] M. Kalimutho, D. Sinha, J. Jeffery, K. Nones, S. Srihari, W. C. Fernando, P. H. Duijf, C. Vennin, P. Raninga, D. Nanayakkara, D. Mittal, J. M. Saunus, S. R. Lakhani, J. A. Lopez, K. J. Spring, P. Timpson, B. Gabrielli, N. Waddell, K. K. Khanna, CEP55 is a determinant of cell fate during perturbed mitosis in breast cancer, EMBO Mol Med, 10 (2018).
[16] J. Leignadier, S. Favre, S. A. Luther, I. F. Luescher, CD8 engineered cytotoxic T cells reprogram melanoma tumor environment, Oncoimmunology, 5 (2016) e1086861.
[17] K. G. Anderson, I. M. Stromnes, P. D. Greenberg, Obstacles Posed by the Tumor Microenvironment to T cell Activity: A Case for Synergistic Therapies, Cancer Cell, 31 (2017) 311-325.
[18] J. A. Rodriguez, HLA-mediated tumor escape mechanisms that may impair immunotherapy clinical outcomes via T-cell activation, Oncol Lett, 14 (2017) 4415-4427.
[19] K. G. Lucas, Q. Sun, R. L. Burton, A. Tilden, W. P. Vaughan, M. Carabasi, D. Salzman, A. Ship, A phase I-II trial to examine the toxicity of CMV- and EBV-specific cytotoxic T lymphocytes when used for prophylaxis against EBV and CMV disease in recipients of CD34-selected/T cell-depleted stem cell transplants, Hum Gene Ther, 11 (2000) 1453-1463.
[20] P. Comoli, S. Basso, M. Zecca, D. Pagliara, F. Baldanti, M. E. Bernardo, W. Barberi, A. Moretta, M. Labirio, M. Paulli, M. Furione, R. Maccario, F. Locatelli, Preemptive therapy of EBV-related lymphoproliferative disease after pediatric haploidentical stem cell transplantation, Am J Transplant, 7 (2007) 1648-1655.
[21] R. Khanna, S. Bell, M. Sherritt, A. Galbraith, S. R. Burrows, L. Rafter, B. Clarke, R. Slaughter, M. C. Falk, J. Douglas, T. Willams, D. J. Moss, Activation and adoptive transfer of Epstein-Barr virus-specific cytotoxic T cells in solid organ transplant patients with posttransplant lymphoproliferative disease, Proc. Natl. Acad. Sci. U.S.A., 1999, pp. 10391-10396.
[22] B. Savoldo, J. A. Goss, M. M. Hammer, L. Zhang, T. Lopez, A. P. Gee, Y. F. Lin, R. E. Quiros-Tejeira, P. Reinke, S. Schubert, S. Gottschalk, M. J. Finegold, M. K. Brenner, C. M. Rooney, H. E. Heslop, Treatment of solid organ transplant recipients with autologous Epstein Barr virus-specific cytotoxic T lymphocytes (CTLs), Blood, 108 (2006) 2942-2949.
[23] M. Vanneman, G. Dranoff, Combining immunotherapy and targeted therapies in cancer treatment, Nat Rev Cancer, 12 (2012) 237-251.
[24] C. Liu, W. Peng, C. Xu, Y. Lou, M. Zhang, J. A. Wargo, J. Q. Chen, H. S. Li, S. S. Watowich, Y. Yang, D. Tompers Frederick, Z. A. Cooper, R. M. Mbofung, M. Whittington, K. T. Flaherty, S. E. Woodman, M. A. Davies, L. G. Radvanyi, W. W. Overwijk, G. Lizee, P. Hwu, BRAF inhibition increases tumor infiltration by T cells and enhances the antitumor activity of adoptive immunotherapy in mice, Clin Cancer Res, 19 (2013) 393-403.
[25] P. J. R. Ebert, J. Cheung, Y. Yang, E. McNamara, R. Hong, M. Moskalenko, S. E. Gould, H. Maecker, B. A. Irving, J. M. Kim, M. Belvin, I. Mellman, MAP Kinase Inhibition Promotes T Cell and Anti-tumor Activity in Combination with PD-L1 Checkpoint Blockade, Immunity, 44 (2016) 609-621.

[26] A. Boni, A. P. Cogdill, P. Dang, D. Udayakumar, C. N. Njauw, C. M. Sloss, C. R. Ferrone, K. T. Flaherty, D. P. Lawrence, D. E. Fisher, H. Tsao, J. A. Wargo, Selective BRAFV600E inhibition enhances T-cell recognition of melanoma without affecting lymphocyte function, Cancer Res, 70 (2010) 5213-5219.

[27] D. T. Frederick, A. Piris, A. P. Cogdill, Z. A. Cooper, C. Lezcano, C. R. Ferrone, D. Mitra, A. Boni, L. P. Newton, C. Liu, W. Peng, R. J. Sullivan, D. P. Lawrence, F. S. Hodi, W. W. Overwijk, G. Lizee, G. F. Murphy, P. Hwu, K. T. Flaherty, D. E. Fisher, J. A. Wargo, BRAF inhibition is associated with enhanced melanoma antigen expression and a more favorable tumor microenvironment in patients with metastatic melanoma, Clin Cancer Res, 19 (2013) 1225-1231.

[28] S. Hu-Lieskovan, S. Mok, B. Homet Moreno, J. Tsoi, L. Robert, L. Goedert, E. M. Pinheiro, R. C. Koya, T. G. Graeber, B. Comin-Anduix, A. Ribas, Improved antitumor activity of immunotherapy with BRAF and MEK inhibitors in BRAF(V600E) melanoma, Sci Transl Med, 7 (2015) 279ra241.

[29] S. H. Kang, B. Keam, Y. O. Ahn, H. R. Park, M. Kim, T. M. Kim, D. W. Kim, D. S. Heo, Inhibition of MEK with trametinib enhances the efficacy of anti-PD-L1 inhibitor by regulating anti-tumor immunity in head and neck squamous cell carcinoma, Oncoimmunology, 8 (2019) e1515057.

[30] A. R. Karpf, D. A. Jones, Reactivating the expression of methylation silenced genes in human cancer, Oncogene, 21 (2002) 5496-5503.

[31] H. J. Kim, S. C. Bae, Histone deacetylase inhibitors: molecular mechanisms of action and clinical trials as anti-cancer drugs, Am J Transl Res, 3 (2011) 166-179.

[32] Y. Kagoya, M. Nakatsugawa, Y. Yamashita, T. Ochi, T. Guo, M. Anczurowski, K. Saso, M. O. Butler, C. H. Arrowsmith, N. Hirano, BET bromodomain inhibition enhances T cell persistence and function in adoptive immunotherapy models, J Clin Invest, 126 (2016) 3479-3494.

[33] J. E. Delmore, G. C. Issa, M. E. Lemieux, P. B. Rahl, J. Shi, H. M. Jacobs, E. Kastritis, T. Gilpatrick, R. M. Paranal, J. Qi, M. Chesi, A. C. Schinzel, M. R. McKeown, T. P. Heffernan, C. R. Vakoc, P. L. Bergsagel, I. M. Ghobrial, P. G. Richardson, R. A. Young, W. C. Hahn, K. C. Anderson, A. L. Kung, J. E. Bradner, C. S. Mitsiades, BET bromodomain inhibition as a therapeutic strategy to target c-Myc, Cell, 146 (2011) 904-917.

[34] S. C. Casey, L. Tong, Y. Li, R. Do, S. Walz, K. N. Fitzgerald, A. M. Gouw, V. Baylot, I. Gutgemann, M. Eilers, D. W. Felsher, MYC regulates the antitumor immune response through CD47 and PD-L1, Science, 352 (2016) 227-231.

[35] M. Kalimutho, D. Sinha, D. Mittal, S. Srihari, D. Nanayakkara, S. Shafique, P. Raninga, P. Nag, K. Parsons, K. K. Khanna, Blockade of PDGFRbeta circumvents resistance to MEK-JAK inhibition via intratumoral CD8 (+) T-cells infiltration in triple-negative breast cancer, J Exp Clin Cancer Res, 38 (2019) 85.

[36] D. E. Johnson, R. A. O'Keefe, J. R. *Grandis*, Targeting the IL-6/JAK/STAT3 signalling axis in cancer, Nat Rev Clin Oncol, 15 (2018) 234-248.

[37]C. S. Tudor, C. W. Dawson, J. Eckhardt, G. Niedobitek, A. C. Buttner, B. Seliger, A. Hartmann, M. Buettner, c-Myc and EBV-LMP1: two opposing regulators of the HLA class I antigen presentation machinery in epithelial cells, Br J Cancer, 106 (2012) 1980-1988.

The invention claimed is:

1. A method of treating or preventing an EBV-associated disease, disorder or condition in a subject, said method includes administering to the subject a composition comprising:

(a) a first population of allogeneic T cells that bind or recognize a first epitope of an EBV antigen;

(b) a second population of allogenic T cells that bind or recognize a second epitope of the EBV antigen or a further EBV antigen;

(c) an immunotherapeutic agent, a MAPK pathway inhibitor, a BET Inhibitor, and any combination thereof; and (d) a pharmaceutically acceptable carrier, diluent, and/or excipient; to thereby treat or prevent the EBV-associated disease, disorder or condition in the subject, wherein the first population of allogenic T cells and EBV-positive cells of an EBV-associated disease in a subject share or are restricted by a first HLA allele encoding a first MHC protein, wherein the second population of allogenic T cells and the EBV-positive cells of the EBV-associated disease in the subject share or are restricted by a second HLA allele encoding a second MHC protein, wherein the first and second HLA alleles are different, and wherein the first and second populations of allogenic T cells do not have the same HLA allele complement.

2. A pharmaceutical compostions for treating or preventing an EBV-associated disease, disorder or condition in a subject, the composition comprising:

(a) a first population of allogeneic T cells that bind or recognize a first epitope of an EBV antigen;

(b) a second population of allogenic T cells that bid or recognize a second epitope of an EBV antigen;

(c) a therapeutic agent, wherein the therapeutic agent is selected from the group consisting of an immunotherapeutic agent, a MAPK pathway inhibitor, a BET inhibitor or a combination thereof; and (d) a pharmaceutically acceptable carrier, diluent, and/or excipient, wherein the first population of allogenic T cells and EBV-positive cells of an EBV-associated disease in a subject share or are restricted by a first HLA allele encoding a first MHC protein, wherein the second population of allogenic T cells and the EBV-positive cells of the EBV-associated disease in the subject share or are restricted by a second HLA allele encoding a second MHC protein, wherein the first and second HLA alleles are different, and wherein the first and second populations of allogenic T cells do not have the same HLA allele complement.

3. The method of claim 1, further including the initial step of generating the first population of allogeneic T cells in vitro.

4. The method of claim 1, wherein the immunotherapeutic agent is or comprises an immune checkpoint inhibitor.

5. The method of claim 1, wherein the MAPK pathway inhibitor is or comprises a MEK1/2 inhibitor.

6. The method of claim 1, wherein the population of allogeneic T cells is administered prior to, simultaneously with and/or subsequent to administration of the therapeutic agent.

7. The method of claim 1, wherein the EBV antigen and/or the further EBV antigen is selected from the group consisting of EBNA1, EBNA2, EBNA3A, EBNA3B, EBNA3C, LMP1, LMP2, and any combination thereof.

8. The method of claim 1, wherein the EBV-associated disease, disorder or condition is or comprises an EBV-associated cancer.

9. The method of claim 8, wherein the EBV-associated cancer is selected from the group consisting of nasopharyngeal carcinoma, NKT cell lymphoma, Hodgkin's Lymphoma, post-transplant lymphoproliferative disease, Burkitt's lymphoma, Diffuse large B-cell lymphoma, gastric cancer, and any combination thereof.

10. The method of claim 1, wherein the EBV-associated disease, disorder or condition is or comprises an EBV-associated cancer or tumor, and wherein:

(a) the first MHC protein presents the first epitope of the EBV antigen on cancer or tumor cells;

(b) the second MHC protein presents the second epitope of the EBV antigen, or the epitope of the further EBV antigen, on cancer or tumor cells; or (c) both (a) and (b).

11. The method of claim 1, further including the initial step of generating the second population of allogeneic T cells in vitro.

12. The composition of claim 2, wherein the EBV antigen and/or the further EBV antigen is selected from the group consisting of EBNA1, EBNA2, EBNA3A, EBNA3B, EBNA3C, LMP1, LMP2 and any combination thereof.

13. The method of claim 4, wherein the immune checkpoint inhibitor is selected from a PD-L1 inhibitor, a CTLA4 inhibitor, a LAG3 inhibitor, a TIM3 inhibitor, or a CD96 inhibitor.

* * * * *